USO05209987A

United States Patent [19]
Penneck et al.

[11] Patent Number: 5,209,987
[45] Date of Patent: May 11, 1993

[54] WIRE AND CABLE

[75] Inventors: Richard J. Penneck, Lechlade; James M. O'Brien, Swindon; Stephen J. Duckworth, Swindon; Nicholas J. G. Smith, Swindon, all of England

[73] Assignee: Raychem Limited, United Kingdom

[21] Appl. No.: 605,868

[22] Filed: Oct. 30, 1990

Related U.S. Application Data

[60] Division of Ser. No. 818,854, Jan. 14, 1986, Pat. No. 4,985,313, and a continuation-in-part of Ser. No. 711,537, Mar. 7, 1985, abandoned.

[30] Foreign Application Priority Data

| Jul. 8, 1983 | [GB] | United Kingdom | 8318612 |
| Jan. 14, 1985 | [GB] | United Kingdom | 8500816 |
| Jan. 14, 1985 | [GB] | United Kingdom | 8500817 |
| Jan. 14, 1985 | [GB] | United Kingdom | 8500818 |
| Jan. 14, 1985 | [GB] | United Kingdom | 8500819 |
| Jan. 30, 1985 | [GB] | United Kingdom | 8502316 |

[51] Int. Cl.$^5$ .................. H01B 1/02; H01B 7/18
[52] U.S. Cl. .................. 428/610; 428/623; 428/629; 428/632; 428/661; 428/674; 428/457; 439/887
[58] Field of Search ............... 428/605, 610, 623, 627, 428/629, 632, 633, 661, 674, 457, 469; 439/887

[56] References Cited

U.S. PATENT DOCUMENTS

| 4,123,595 | 10/1978 | Chang | 428/610 |
| 4,399,199 | 8/1983 | McGill et al. | 428/633 |
| 4,481,237 | 11/1984 | Bosshart et al. | 428/610 |
| 4,503,130 | 3/1985 | Bosshart et al. | 428/610 |
| 4,535,033 | 8/1985 | Stecura | 428/633 |
| 4,588,655 | 5/1986 | Kushner | 428/633 |
| 4,985,313 | 1/1991 | Penneck et al. | 428/629 |

FOREIGN PATENT DOCUMENTS

| 659977 | 10/1951 | United Kingdom . |
| 1179896 | 2/1970 | United Kingdom . |

*Primary Examiner*—George Wyszomierski
*Attorney, Agent, or Firm*—Herbert G. Burkard; Sheri M. Novack

[57] ABSTRACT

An article of manufacture, for example a conductor for an electrical wire or cable, is provided with a refractory coating preferably formed from a refractory metal or semi-metal oxide or nitride and preferably deposited on the surface of the article by a vacuum deposition process such as a sputter ion plating method. Adhesion of the refractory coating, especially at high temperatures may be improved, and migration of the substrate metal through the coating may be suppressed by varying the stoichiometry of the coating through its thickness and-/or by the provision of a metallic or refractory intermediate layer. The articles are particularly suitable for use in circuit and signal integrity cables.

The vacuum deposited refractory layer may constitute the sole refractory, or additional refractory layers may be deposited by other methods e.g. a sol-gel method.

27 Claims, 7 Drawing Sheets

WIRE AND CABLE

This application is a division of application Ser. No. 06/818,854 filed Jan. 14, 1986, now U.S. Pat. No. 4,985,313, which is a continuation-in-part of application Ser. No. 06/711,537, filed Mar. 7, 1985, now abandoned.

This invention relates to articles that are formed from metals such as electrical components, and especially to electrical wire and cables and to electrical conductors suitable for use therein.

Numerous forms of electrical cable have been proposed for use in environments where there is a risk of fire and accordingly where fire retardency of the cable is required. These cables may make use of specific, highly effective, halogenated polymers or flame retardant materials such as polytetrafluoroethylene, polyvinyl chloride, or polyvinylidine fluoride as polymers or decabromodiphenyl ether as flame retardant additives. Halogenated systems, however, suffer from the disadvantage that when they are heated to high temperatures during a fire, they liberate toxic and corrosive gases such as hydrogen halides, and a number of halogen free insulating compositions have therefore been proposed, for example in U.S. Pat. No. 4,322,575 to Skipper and in U.K. patent specification Nos. 1,603,205 and 2,068,347A, the disclosures of which are incorporated herein by reference.

One area in which the present invention is particularly applicable is that of electrical wires and cables. For example so called "magnet wire" which is used in electromagnet windings in transformers, motors and other equipment, may experience severe temperature excursions under overload conditions in service. In certain fields where cables are used, for example in military, marine or mass transit applications, it is desired to use cables which are capable of functioning at relatively high temperatures. In other instances it is desired to use cables which not only do not burn, or, if they burn, do not liberate toxic or corrosive gases, but also are capable of functioning after having been subjected to a fire, or preferably for a period of time during a fire without shorting or otherwise failing. Cables that are capable of functioning for a period of time during a fire have been called circuit integrity cables or signal integrity cables depending on their use. The previously proposed circuit and signal integrity cables have generally used the principle that the individual conductors should be separated from one another by mica tapes or by large volumes of packing materials or silicones or by combinations thereof in order to prevent the formation of short circuits during a fire, with the result that the previously proposed cables are relatively heavy or large or both. There is therefore a need for a cable that will function at relatively high temperatures or will function after it has been subjected to a fire, and which preferably will retain its integrity for a period of time during a fire but which is smaller or lighter than the previously proposed cables.

According to one aspect, the present invention provides an electrical wire which comprises an elongate metallic electrical conductor having an adherent electrically insulating refractory coating formed from a compound of a metal or semi-metal other than that from which the conductor is formed, e.g. an oxide or nitride, the refractory coating having been formed on the conductor by a vacuum deposition method, and, surrounding the coated conductor, a layer of polymeric insulation.

Preferably the refractory coating is bonded to the conductor by a metallic or refractory intermediate layer, and so according to another aspect, the invention provides an electrical wire which comprises an elongate metallic conductor having an adherent refractory coating which is bonded to the conductor by a metallic or refractory intermediate layer, and which has preferably been formed by a vacuum deposition method, and, surrounding the coated conductor, a layer of polymeric insulation.

Preferably the metal forming the conductor has a melting point of at least 800° C. more preferably at least 900° C., and especially at least 1000° C., the most preferred metal being copper although in some instances it is possible for the conductor to have a melting point below 800° C., for example it is possible for the conductor to be formed from aluminium if the required temperature rating of the wire is not particularly high. The conductor may be a solid conductor or it may be a stranded conductor in which individual strands are laid together to form a bundle which preferably contains 7, 19 or 37 strands. Where the conductor is stranded it is preferred for the bundle to be coated rather than the individual strands, that is to say, the refractory coating extends around the circumference of the bundle but not around the individual strands so that substantially only the outwardly lying surfaces of the outermost layer of strands are coated. Thus, according to another aspect, the invention provides a metallic conductor which comprises a bundle of metallic strands the bundle having an adherent coating of an electrically insulating refractory oxide or nitride of a metal or semi-metal which extends around the circumference of the bundle but not around the individual strands. This form of conductor has the advantage that the inter strand electrical contact is retained and the dimensions of the bundle are kept to a minimum (since the thickness of the coating may constitute a significant proportion of the strand dimensions for fine gauge conductors) and also it aids the formation of good electrical connections, e.g. crimp connections, to the conductor because a large proportion of the surface of the strands, and the entire surface of the strands in the central region of the conductor, will be uncoated.

The wire according to the invention, at least in its preferred aspects described below, is particularly suitable for forming signal integrity cables and circuit integrity cables because, depending on the construction of the wire, when a portion of the cable is subjected to a fire, the refractory coating will provide sufficient insulation between the conductors to enable the cable to operate for a significant length of time even when all the polymeric insulation has been lost. The length of time for which the wire will still operate will clearly depend on the temperature to which it is subjected, and, in fact, in view of the refractory nature of the insulating coating, the temperatures at which some of the wires and cable according to the invention can operate at least for short periods of time is limited only by the nature of the metal forming the conductor.

An additional advantage of the wire and cable according to the invention is that it is very flexible as compared with other signal and circuit integrity cables, especially if a stranded conductor is used. The ability of the wire to be bent around very tight bends (small bend radii) without deleterious effect is partly due to the fact that the layer providing the integrity is thinner than with other signal and circuit integrity cables. However, when the conductor is a stranded conductor it may be bent around extremely tight bends without undue stress on the surface of the stands because the strands are displaced from a regular hexagonal packing at the apex of the bend thereby exposing uncoated areas of the strands to the eye. It is highly surprising that even though uncoated strands may be exposed when the wire conductor is bent there is no electrical contact between adjacent stranded conductors after the polymeric insulation has been removed. It is believed that in this case the integrity is retained because the profile of a stranded conductor is not cylindrical but rather is in the form of a hexagon that rotates along the length of the conductors, so that adjacent stranded conductors will touch one another only at a few points along their length, which points are always provided by the outwardly oriented part of the surface of the strands in the outer layer of the conductors. It is these points of contact that are always provided with the refractory coating.

The refractory coating preferably has a thickness of at least 0.5, more preferably at least 1 and especially at least 2 micrometers but preferably not more than 15 and especially not more than 10 micrometers, the most preferred thickness being about 5 micrometers depending upon specific operational requirements. The exact thickness desired will depend on a number of factors including the type of layer and the voltage rating of the wire, circuit integrity cables usually requiring a somewhat thicker coating than signal integrity cables and sometimes above 15 micrometers. The lower limits for the coating thickness are usually determined by the required voltage rating of the wire whilst the upper limits are usually determined by the time, and there fore the cost, of the coating operation.

Preferably the insulating refractory coating is formed from an electrically insulating infusible or refractory metal or semi-metal oxide or nitride and the invention will be described below in many cases with respect to oxides and nitrides although othe refractory coatings are included. By the term "infusible" or "refractory" is meant that the coating material in its bulk form should not fuse or decompose when subjected to a temperature of 800° C., for 3 hours. Preferably the oxide or nitride should be able to withstand higher temperatures also, for example it should be able to withstand a temperature of 1000° C. for at least 20 to 30 minutes. The preferred oxides and nitrides are those of aluminium, titanium, tantalum and silicon or mixtures thereof with themselves or with other oxides or nitrides. Thus, for example, the use of mixed metal oxides for the refractory coating are also encompassed by the present invention. It should be appreciated that the oxide or nitride layer need not, and in many cases will not, have a precisely defined stoichiometry. In a number of cases, depending on the method of forming the refractory coating, the coating will contain the metal or semi-metal in a stoichiometric excess, that is to say, the coating will contain more metal than is required for the stoichiometry of a defined formal oxidation state of the metal. Accordthe terms "aluminium oxide", "titanium oxide", "tantalum oxide", "silicon oxide", "metal oxide" and the equivalent terms when referring to nitrides are intended to include non-stoichiometric compounds. It is often advantageous for the refractory coating to be non-stoichiometric since this may increase the adhesion between the refractory coating and the conductor or any underlying layer, and especially if the stoichiometry of the refractory coating varies through at least part of its thickness so that stresses that may be induced in the coating, for example due to differential thermal expansion, are not localised to a boundry of the coating and so that different parts of the coating will exhibit different properties. For example, a relativmetal-rich part of the coating may exhibit good adhesion to the conductor or intermediate layer while part of the coating having least metal or semi-metal may exhibit the best electrical properties.

Thus, according to another aspect, the invention provides an elongate metallic electrical conductor having an adherent coating of a refractory oxide or nitride of a metal or semi-metal, the coating having a stoichiometry that varies through at least part of its thickness such that the proportion of oxygen or nitrogen increases toward the outer surface of the coating. If desired, the stoichiometry of the refractory coating may vary continuously throughout the thickness of the coating or it may contain one or more layers or strata of relatively uniform stoichiometry. Thus the coating may have an outer region of relatively uniform stoichiometry and preferably of a relatively high oxygen or nitrogen content in order to exhibit the optimum electrical properties. The relative thicknesses of the non-uniform and uniform layers may vary widely. For example the major part of the coating may have a non-uniform stoichiometry or the major part of the coating's thickness may be of uniform stoichiometry, in which latter case the non-uniform part of the coating could even be considered as an intermediate layer that improves adhesion of the coating especially at high temperatures. If the underlying metal or semi-metal-rich part of the coating is intended to improve the adhesion of the refractory coating, its particular composition will depend on the composition of any underlying layer, and in some cases it may be desirable for the metal or semi-metal rich part to consist substantially entirely of the metal or semi-metal so that there is a gradual change from the metal or semi-metal to the oxide or nitride. This is particularly preferred if the system includes an intermediate layer of the same metal or semi-metal.

The precise stoichiometry of the uniform top layer can be determined experimentally using wavelength dispersive electron microprobe analysis or by using x-ray photoelectron spectroscopy (XPS). The composition of the coating as it changes from metal to refractory throughout its depth can be assessed using Auger electron spectroscopy (AES) in which the film is continuously sputtered away to expose fresh surface for composition analysis.

The variation in stoichiometry is not limited to a variation in the metal or semi-metal/oxygen or nitrogen proportions. In addition or alternatively the relative proportions of two different metals or semi-metals may be varied so that, for example, there is a gradual change from one metal, which may constitute an intermediate layer, to the oxide or nitride of a different metal.

The outer region of the refractory coating preferably has a molar oxygen or nitrogen content that is at least 50%, more preferably at least 65% and especially at least 80% of the oxygen or nitrogen content of a defined stable formal oxidation state of the metal. Thus the preferred oxide composition of the outer region may be represented as $MO_x$ where x is at least 0.75, preferably at least 1 and especially at least 1.25 in the case of aluminium, at least 1, preferably at least 1.3 and especially at least 1.5 in the case of titanium or silicon, and
at least 1.25, preferably at least 1.6 and especially at least 2 in the case of tantalum.

For relatively thin refractory coatings that have a stoichiometric excess of the metal or semi-metal it has been found that the coating remains insulating as the temperature is raised up to a certain temperature, usually in the range of 300° to 600° C. and then becomes conductive when a load of 30 V is applied. In general the electrical properties of the coatings, as determined by the temperature of onset of conductivity, may be improved both by increasing the thickness of the coating and by increasing the oxygen or nitrogen content thereof although to some extent either the thickness or the oxygen or nitrogen content may be increased at the expense of the other.

Although it is possible, at least in the broadest aspect of the invention, for the refractory coating to consist of a single layer only which is deposited on the conductor, it is possible, and in may cases preferable, for one or more additional layers to be formed. For example a refractory coating comprising an oxide may have a refractory nitride layer thereon. Examples of nitrides that may be deposited on refractory coatings to improve the mechanical properties include titanium nitride or aluminium nitride.

Other examples of additional layers that may be exployed are metallic or refractory intermediate layers located between the conductor and the refractory oxide or nitride coating as mentioned above. Metallic intermediate layers may be present in order to improve the adhesion between the refractory coating and the conductor and include those metals from which the refractory coating is formed or other metals or both. Preferred metallic intermediate layers include those formed from aluminium, titanium, tantalum or silicon although other metals, e.g. nickel, silver or tin may be used, which may have been previously applied to the conductor by conventional techniques. Thus, for example, while copper is the preferred metal for forming the conductor, a silver plated steel wire may be used if the wire is intended to carry very high frequency signals.

It has been found that articles according to the invention are highly resistant to high temperatures and that the integrity of the refractory coating is not destroyed at high temperatures for relatively long periods of time. By examination of articles in accordance with the present invention and articles in which no, or only a thin, intermediate metal layer is present, by means of a scanning electon microscope, it has been observed that the predominant failure mechanism of articles having no intermediate layer is through spalling. When articles are provided with a thicker metal intermediate layer the spalling is reduced and failure occurs through a mechanism in which the underlying copper appears to migrate through the refractory layer and appear at the outer surface of the refractory layer, in the form of small globules or a network of "dykes" or in other cases, in the form of "blisters". This form of failure may occur at temperatures as low as 500° C., well below the melting point of copper. The particular reason why this failure occurs is unclear and it is likely that more than one mechanism is responsible for the failure in different cases. One theory as to the failure mechanism is that, at elevated temperatures, the underlying copper is oxidized by ambient oxygen which has penetrated the refractory layer, either by diffusion or through cracks that may have been caused by mechanical or thermal stresses in the refractory layer, to form copper oxide ($Cu_2O$ or $CuO$) which are relatively electrically conductive. Growth of the copper oxide scale would proceed by outward diffusion of copper through the copper oxide to combine with inwardly diffusing oxygen until it reached the outer surface of the refractory layer. In the case of circuit integrity wires electrical integrity of the system would be significantly deleteriously affected.

Whatever the precise failure mechanism is, and whether the underlying copper migrates through the refractory layer in its elemental form or in the form of its oxide, it has been observed that this migration may be significantly reduced or prevented by the provision of an intermediate layer which is preferably relatively thick and acts as a barrier to diffusion of oxygen or copper or both.

It has also been observed that thick intermediate layers can act to reduce or eliminate crack formation resulting from the thermal expansion mismatch between copper and the refractory layer, and so improve the temperature resistance of the article.

This failure mechanism, and the solution to the failure mechanism is applicable to a wide range of articles in which refractory coatings are provided for thermal protection, mechanical protection, corrosion protection and the like. Examples of such articles include electrical connectors, mechanical couplings casings and the like. Accordingly, yet another aspect of the invention provides an article of manufacture that is formed at least partly from a metal and has, on at least part of a metallic surface thereof, an adherent refractory coating for protecting the article, wherein the refractory coating has a stoichiometry that varies such that the proportion of metal in the refractory coating increases toward the surface of the underlying metallic article and/or the coating is bonded to the article by means of an intermediate metallic or refractory layer, so that migration of underlying metal of the article through the refractory coating when the article is heated is suppressed.

The present invention also provides an article of manufacture which has at least a part that is formed from metallic copper, the article having, on a surface of that part, an adherent, substantially contaminant-free refractory layer and an intermediate layer formed from a metal which acts as a barrier to diffusion of oxygen or copper or both, the intermediate layer having a thickness of at least 1.1, preferably at least 1.2, more preferably at least 1.5, especially at least 2 and most especially at least 3 micrometers.

It has been found that, in articles according to the invention the metal forming the intermediate layer eliminates or substantially reduces the mechanisms by which failure occurs, thus extending the high temperature lifetime of the article. Thus, for example in the case of circuit or signal integrity cables the time required to cause circuit failure in a fire would be substantially increased. The metal forming the intermediate layer for this purpose may be one which acts as a barrier to diffusion of either the underlying substrate to the outer surface of the article or to the diffusion of oxygen into the substrate. It may restrict diffusion in its elemental form or it may hinder diffusion processes, by formation of oxide scales when exposed to air, as is the case with for example Aluminium. Such scales are most effective if they are stable on formation and exhibit low growth rates. The intermediate layer may be formed of metals which will alloy with the underlying substrate on exposure to high temperatures but which would still preferentially oxidise to form stable scales on exposure to air, or may be formed from metallic alloys which exhibit high oxidative stability e.g. titanium/aluminium alloys. The metal forming the intermediate layer may also be selected to take advantage of physical or chemical compatibility with the substrate and refractory layers to maximise adhesion.

In addition it has been found that in many cases the provision of a relatively thick intermediate layer significantly reduces the formation of cracks in the refractory layer when the article is subjected to mechanical abuse. It is believed that the reduction in formation of cracks is due to the change in stress distribution in the refractory layer when the article is subjected to strain by virtue of the deformation of the intermediate layer. Thus, according to another aspect, the present invention provides an article of manufacture which has at least a part that is formed from metallic copper, the article having on a surface of that part, an adherent substantially contaminant-free, refractory layer and an adherent intermediate layer formed from a metal that has a lower modulus than that of copper (for example aluminium), the intermediate layer having a thickness of at least 1.1 micrometers. Since the absolute value of the modulus will depend on the strain, for strains beyond the limit of proportionality, and on the morphology of the material, the modulus as used herein refers to an arbitary value of 1% strain and for the annealed material in its bulk form.

In some cases it is possible for a single metal intermediate layer both to have a lower modulus than that of copper and to act as a diffusion barrier to copper and/or oxygen, while in other instances more than one intermediate layer may be provided, for example one layer acting as a diffusion barrier and the other layer acting as a stress relieving layer or keying layer. For example a copper article may be provided with a nickel diffusion barrier intermediate layer and, on the nickel layer, an aluminium stress relieving/keying layer.

In the case in which the article has more than one intermediate layer, it is possible in many cases for the intermediate layers to be relatively thin since the layers may be chosen from different materials that optimise specific properties, and so, according to another aspect, the invention provides an article of manufacture which has at least a part that is formed from metallic copper, the article having on a surface of that part, an adherent substantially contaminant free, electrically insulating refractory layer and at least two intermediate layers, at least one of the intermediate layers acting as a diffusion barrier and/or a strain-relieving layer and/or a keying layer. For example, at least one of the intermediate layers may act as a barrier to the diffusion of copper and/or oxygen while the or at least one other layer may act as a strain-relieving layer and/or keying layer.

As stated above, the refractory layer is substantially contaminant-free, that is to say, the refractory layer contains only those species that are intended in order for the layer to fulfill its intended function, and contains substantially no species that result from the manufacturing process. An important feature of the refractory layer is good control of composition to optimise the high temperature performance of the article. The composition is totally inorganic and therefore does not rely on conversion processes to occur during exposure to normal or emergency high temperature service, as is the case for example in many mica filled or glass filled silicone resin systems. The composition is also improved by removing the use of polymeric binders to support inorganic materials which may be consolidated by firing processes to form the inorganic insulation. Similarily, articles in which the refractory coatings, or at least the have been formed by electrochemical conversion of metal layers e.g. by anodising an aluminium layer, do not form part of the invention, such layers often being heavily contaminated with ionic residue from the electrolytic solutions e.g. sulphates from sulphuric acid anodisation processes. Such wet chemical processes may result in contamination of the intermediate layer described above. Suitable deposition techniques include physical vapour deposition processes such as reactive evaporation and sputtering or plasma assisted chemical vapour deposition. Coatings can also be formed by plasma oxidation of the metals or by non vacuum processes such as a high pressure CVD method, the refractory layer preferably being deposited at a temperature of not more than 350° C.

In the case of electrical equipment the refractory layer may provide the entire electrical insulation or one or more additional insulating layers may be provided thereon. The additional insulating layer may be inorganic or organic or a combination of inorganic and organic layers may be provided.

In the case of a stranded conductor in which the conductor bundle (rather than the individual strands) is provided with a refractory coating, the problem of growth of cuprous oxide scale is particularly severe since it is inevitable that some cracking of the refractory coating will occur in the regions between the strands and ambient air will be able to penetrate into the interstices of the strands which, in turn, causes cuprous oxide scale to swell out of the conductor between the strands. This problem may be overcome or substantially reduced according to the invention by providing an intermediate metal layer around the individual strands, which acts as a barrier to diffusion of oxygen or copper or both.

Thus according to another aspect, the present invention provides an electrical wire having a conductor which comprises a bundle of copper strands, the bundle having an adherent, electrically insulating, refractory coating which extends around the circumference of the bundle but not around the individual strands, and the individual strands having an intermediate layer extending around them, the intermediate layer being formed from a metal which acts as a barrier to diffusion of oxygen or copper or both and preferably having a thickness of at least 1.5 micrometers.

In certain cases the ability of the stranded conductor to withstand high temperatures may be substantially improved by the provision of a further metallic layer between the intermediate layer and the refractory layer. For example the temperature resistance of a wire having a nickel intermediate layer and an alumina refractory coating may be considerably increased by interposing an additional layer of aluminium between the nickel and the alumina. It has been observed that the improvement is due to a further reduction of the copper migration described above. Thus, according to another aspect, the present invention provides an electrical wire having a conductor which comprises a bundle of copper strands, the bundle having an adherent, electrically insulating, refractory coating that extends around the bundle but not around the individual strands, and the individual strands having an intermediate layer extending around them, the intermediate layer being formed from a metal which acts as a barrier to diffusion of oxygen or copper or both, the conductor including an additional metallic layer between the intermediate layer and the refractory coating. It has also be observed that the provision of a relatively thick intermediate layer and/or further metallic layer can act to reduce or eliminate crack formation resulting from the thermal expansion mismatch between the copper and the refractory layer.

The additional metallic layer may, if desired, extend around the individual strands of the conductors or it may be, and preferably is, present only in those areas that are provided with the refractory coating. For example, it is preferably provided around the conductor only when the individual strands have been laid up to form the stranded conductor. This layer may be applied in the same way as the other metallic intermediate layer although the particular method that is used may depend on whether the additional layer extends around the individual strands or around the bundle as a whole. Where the additional layer extends round the bundle as a whole vacuum deposition techniques e.g. sputter plating are preferred. In this case the intermediate layer and the additional layer may comprise the same metal, so that each strand is enclosed within a metal layer that is thicker on the outwardly facing surfaces of the outer strands. The preferred metal for the intermediate layer in this construction is nickel and for the additional layer, aluminium or nickel are preferred.

In the case of the stranded conductor, the intermediate layer and/or any additional metallic layer preferably each has a thickness of at least 0.3, more preferably at least 1, especially at least 1.5 and most especially at least 3 micrometers, the temperature stability of the refractory layer increasing markedly with increasing thickness of the intermediate and/or additional layer.

All the compositions, structures and processes described herein are applicable to such articles.

More than one intermediate layer may be provided on the conductor if desired, for instance a barrier layer may be provided between the conductor and the other intermediate layer or an alloy layer may be formed from a deposited metal and the conductor metal (e.g. Aluminium/copper) during manufacture, or in a subsequent heating step or in high temperature use. In at least some cases the provision of an alloy layer significantly improves adhesion of the coating.

In the case of wires according to the invention, the polymeric insulation is provided in order to provide additional insulation to the conductor during normal service conditions and also to enable the wire to have the desired dielectric properties and other properties e.g. mechanical properties, scuff resistance, colour coding ability etc. However, an important advantage of the present invention is that since a significant proportion of or all the service insulating properties are provided by the refractory coating, the electrical properties of the polymeric insulation are not as critical as with other wire contructions in which the polymeric insulation provides the sole insulation between the conductors. Of the known polymeric materials that are used for electrical insulation, polyethylene probably has the most suitable electrical properties but is highly flammable, and has poor mechanical properties. Attempts to flame retard polyethylene have either required halogenated flame retardants which, by their nature, liberate corrosive and toxic hydrogen halides when subjected to fire, or have required relatively large quantities of halogen free flame retardants which have a deleterious effect on the electrical properties and often also the mechanical properties of the polymer. Accordingly, an acceptable wire has in the past only been achieved by a compromise between different properties which is often resolved by using a relatively thick-walled polymeric insulation and/or dual wall constructions. Although such forms of polymeric insulation may be used with the wire according to the present invention, the presence of the refractory layer does obviate these problems to a large extent since the polymer used for the insulation may be chosen or its flammability and/or its mechanical properties at the expense of its electrical properties. As examples of polymers that may be used to form the polymeric insulation there may be mentioned polyolefins e.g. ethylene homopolymers and copolymers with alpha olefins, halogenated polymers e.g tetrafluoroethylene, vinylidene fluoride, hexafluoropropylene and vinyl chloride homo or copolymers polyamides, polyesters, polyimides, polyether ketones e g. polyarylether ketones, aromatic polyether imides and sulphones, silicones, alkene/vinyl acetate copolymers and the like. The polymers may be used alone or as blends with one another and may contain fillers e.g. silica and metal oxides e.g. treated and untreated metal oxide flame retardants such as hydrated alumina and titania. The polymers may be used in single wall constructions or in multiple wall constructions, for example a polyvinylidine fluoride layer may be located on for example a polyethylene layer. The polymers may be uncrosslinked but preferably are crosslinked, for example by chemical cross-linking agents or by electron or gamma irradiation, in order to improve their mechanical properties and to reduce flowing when heated. They may also contain other materials e.g. anti-oxidants, stabilizers, crosslinking promotors, processing aids and the like. It is particularly preferred for the polymeric insulation to contain a filler e.g. hydrated alumina, hydrated titania, dawsonite, silica and the like, and especially a filler that has the same chemical composition, at least under pyrolysis conditions, as the refractory coating, so that the filler in the polymeric insulation will provide additional insulation when the wire or cable is subjected to a fire. Another preferred type of polymeric insulation is one that will char, for instance certain aromatic polymers mentioned above, or that will ash e.g. a silicone polymer, when subjected to a fire so that the char or ash, together with the refractory coating, will provide the necessary insulation during a fire. Examples of polymers, compositions, their manufacture and wires using them are described in U.S. Pat. Nos. 3,269,862, 3,580,829, 3,953,400, 3,956,240, 4,155,823, 4,121,001 and 4,320,224, British Patent Specifications Nos. 1,473,972, 1,603,205, 2,068,347 and 2,035,333, 1,604,405 and in European Patent Specification No. 69,598, the disclosures of which are incorporated herein by reference. Preferably the wire is substantially halogen free.

The metallic intermediate layer may be formed in a number of ways, for instance by electroplating, standard wire cladding techniques such as roll bonding or by coating from a metal melt, and by vacuum deposition techniques e.g. sputtering, evaporation, flame spraying, plasma assisted chemical vapour deposition (CVD) or other techniques. Preferably the intermediate layer is formed at a temperature of not more than 150° C.

At least for certain aspects of the present invention, the oxide layer may be applied to the conductor by any of a number of techniques. For example a metal layer may be deposited and then oxidized, e.g. an aluminium layer may be formed and then anodized. Alternatively the metal may be oxidised in a commercially available plasma oxidation unit. The formation of the metal layer may be achieved in a number of ways, for instance by electroplating, standard wire cladding techniques such as roll bonding, and by vacuum deposition techniques e.g. sputtering, evaporation, flame spraying, plasma assisted chemical vapour deposition (CVD) or other techniques. Alternatively the coating may be formed by a plasma ashing technique in which the metallic conductor is coated with, for example, a titanate or siloxane resin and is then passed through an oxygen glow discharge plasma whereupon the resin is "ashed" to leave a coating of titanium dioxide or silica on the conductor.

A vacuum deposition method such as evaporation, plasma assisted chemical vapour deposition, or especially a sputtering method is preferred for forming the refractory layer.

In the sputtering method, predominantly neutral atomic or molecular species are ejected from a target, which may be formed from the material to be deposited, under the bombardment of inert gas positive ions e.g. argon ions. The high energy species ejected will travel considerable distances to be deposited on the wire conductor substrate held in a medium vacuum, e.g. $10^{-4}$ to $10^{-2}$ mbar. The positive ions required for bombardment may be generated in a glow discharge where the sputtering target serves as the cathode electrode to the glow discharge system. The negative potential (with respect to ground and the glow discharge) is maintained in the case of insulating target materials by the use of radio frequency power applied to the cathode, which maintains the target surface at a negative potential throughout the process. DC power may be applied when the target is an electrically conducting material. The advantage of such techniques is that control of the target material is greatly enhanced, and the energy of the species ejected is very much higher than with evaporation methods e.g. typically 1 to 10 eV for sputtering as compared with 0.1 to 0.5 eV for evaporation methods. Considerable improvements in interfacial bonding are achieved but the deposition rate in the sputtering process described will be lower than that for electron beam evaporation.

In magnetron sputtering processes the plasma is concentrated immediately in front of the cathode (target) by means of a magnetic field. The effect of the magnetic field on the gas discharge is dramatic. In that area of discharge where permanent magnets, usually installed behind the cathode, create a sufficiently strong magnetic field vertically to the electric field, secondary electrons resulting from the sputter bombardment process will be deflected by means of the Lorenz force into circular or helical paths. Thus the density of electrons immediately in front of the cathode as well as the number of ionised argon atoms bombarding the cathode are substantially increased. There is an increase in plasma density and a considerable increase in deposition rate. Bias sputtering (or sputter ion plating) may be employed as a variation of this technique. In this case the wire conductor is held at a negative potential relative to the chamber and plasma. The bombardment of the wire conductor by Argon ions results in highly cleaned surfaces. Sputtering of the target material onto the wire conductor thoughout this process results in a simultaneous deposition/cleaning mechanism. This has the advantage that the interfacial bonding is considerably improved. In sputter ion plating systems both substrate and the wire conductor are held at a negative potential. In this case the relative potentials are balanced to promote preferential sputtering of the target material. The target voltage will be typically less than 1 kV, dependant on system design and target material. The wire substrate, may be immersed in its own localised plasma dependant upon its bias potential, which will be lower than that of the target. The exact voltage/power relationship achieved at either target or substrate is dependant upon many variables and will differ in detail from system to system. Typical power densities on the target are 10–20 W/cm$^2$. The load to the substrate may be substantially lower, often as little as 5% of the target load.

The preferred technique that is used to apply the oxide or nitride coating is a reactive bias sputtering method in which reactive gas is introduced into the vacuum chamber in addition to argon so that the oxide/nitride of the target material, which in this case is a metal or semi-metal rather than the oxide/nitride will be deposited. Experimental results have shown that the level of reactive gas and its admission rate have a significant effect on deposition rates. The precision control of partial pressure of the reactive gas and the analysis of the sputtering atmosphere in a closed loop control system is considered highly desirable. Apart from the simultaneous deposition/cleaning advantages mentioned above, the ion bombardment of the substrate enhances surface reaction between the reactive gas and depositing species, resulting in more efficient formation of the coating with the required stoichiometry.

Partial pressure of reactive gas is determined experimentally but will normally be between 2 and 25% but sometimes up to 30%, the exact level depending on the required stoichiometry of the coating and depostion rate. Reactive sputtering is also the preferred technique because it facilitates alterations to the stoichiometry of the coating. For example, an intermediate "layer" of the pure metal used for the oxide/nitride coating may be deposited in such a way that there is no defined boundary between the conductor metal, oxide/nitride metal and oxide/nitride layers.

The vacuum chambers and ancillary equipment, including micro-processor gas control units and a variety of targets used in these methods may be purchased commercially. Many variations in design are possible but most employ the use of "box" shaped chambers which can be pumped down to high vacuum for use in any of the vacuum deposition processes mentioned. Systems are normally, but not exclusively, dedicated to one deposition process. One system which may be employed to coat wire uses air to air transfer techniques for passage of the wire conductor through the deposition chambers and employs one or more ancilliary vacuum chambers either side of the main deposition chamber.

These ancillary chambers are held at progressively higher pressures as they extend from deposition chamber to air. This reduces the load on individual vacuum seals. The system described has the advantage of continuous feed of the wire conductor over batch process arrangements. In the vacuum deposition chamber the pressure is held constant at a pressure normally between $10^{-4}$ and $10^{-2}$ Torr.

The targets employed are commerically available Planar Magetron Sputtering sources. Their size may vary widely, and targets in excess of 2 meters in length may be employed. Between two and four such sources may be arranged opposite one another so as to surround the wire conductor passing through the chamber or to sputter from at least two sides. The arrangement may be employed in series to increase wire throughput rates. As described above a negative bias is applied to the magnetron to initiate the sputtering process. The wire may be held at a lower negative bias as described earlier.

Refinements to the system can, if desired, be employed. For example, the use of an intermediate vacuum station between the air (input side) and the deposition chamber may be employed to generate an Argon ion glow discharge which cleans the wire conductor suface by ion bombardment prior to its entry into the vacuum deposition chamber and also heats the wire conductor.

Further intermediate chambers can be employed between the cleaning and deposition chamber to deposit intermediate layers.

Conditions may be controlled to produce any of the conductor coatings described above in which no defined boundries occur between the layers. For example an intermediate "layer" of the pure metal used for the refractory coating may be deposited in such a way that there is no defined boundry between the conductor metal, the intermediate layer and the oxide or nitride coating. In a similar fashion additional chambers can be employed between the deposition chamber and air (output side) to deposit different metal, metal oxide or metal alloys onto the refractory coating for improved lubrication or wear resistance.

Evaporation and the related processes of activated evaporation and ion plating offer alternative technical for deposition of the coating, with significant advantages in deposition rate.

Evaporation of the coating material is achieved by heating the material such that its vapour pressure exceeds $10^{-2}$ mbar. Evaporation temperatures vary according to coating material, e.g. 1300°-1800° C. or even up to 3500° C. for refractory metal oxides, the chamber pressure being usually $10^{-4}$ to $10^{-6}$ mbar. Similar wire transport systems to those described may be used to hold the substrate about 30-40 cm above the source. Several heating methods exist e.g. resistive, inductive, electron beam impingement etc. although the preferred method is an electron beam source where a beam of high energy electrons e.g. 10,000 eV impinge onto the coating material contained in a water-cooled crucible. The use of multi-pot crucibles or twin source guns, enable multiple layers and graded stoichiometry layers to be deposited with the aid of electronic monitoring and control equipment.

Compound coatings can be made either by direct evaporation from that compound e.g. $Al_2O_3$ or by reactive evaporation, e.g. aluminium evaporated into a partial pressure of oxygen to give aluminium oxide. Variations in the process exist either to promote reactions or adhesion, e.g. Activated reactive evaporation (ARE) can be used to increase the reaction probably between the evaporant and the reactive gas.

In ion-plating, negative bias applied to the substrate in an inert gas, promotes simultaneous cleaning/deposition mechanisms for optimising adhesion as described in the sputtering process. Bias levels of $-2$ KV are typically used but these can be reduced to suit wire substrates. Alternatively, high bias can be applied to a plate positioned behind the traverse wire to achieve a similar effect. As operating pressures are higher in the ion plating technique, e.g. $10^{-3}$ to $10^{-2}$ mbar, gas scattering results in a more even coating distribution. To protect the filament the electron beam gun in the ion plating technique is differentially pumped to maintain vacuum higher than $10^{-4}$ mbar.

In the Plasma assisted chemical vapour deposition (PACVD) method the substrate to be coated is immersed in a low pressure (0.1 to 10 Torr) plasma of the appropriate gases/volatile compounds. This pressure is maintained by balancing the total gas flow-rate against the throughput of the pumping system. The plasma is electrically activated and sustained by coupling the energy from a power generator through a matching network into the gas medium. Thin films have been successfully deposited from direct current and higher frequency plasmas well into the microwave range. At high frequencies the energy may be capacitatively or inductively coupled depending on chanber design and electrode configuration. Typically a 13.56 MHz radiofrequency generator would be used having a rating which would allow a power density of between 0.1-10 W/cm$^2$ in a capacitatively coupled parallel-plate type reactor. The substrate, which could be set at a temperature of up to 400° C., may be grounded, floating or subjected to a dc voltage bias as required. Typically deposition rates for this technique can be favourably compared with those obtained by sputtering. The deposition of alumina may be achieved by immersing a substrate in a plasma containing a volatile alumina compound (e.g. Tri-methyl aluminium or Aluminium butoxide) and oxygen under appropriate processing conditions.

After the oxide coating has been deposited on the wire conductor the polymeric insulation may be extruded onto the coated conductor by methods well known in the art.

In order to form a circuit or signal integrity on cable the appropriate wires according to the invention may simply be laid together and be enclosed in a jacket. If desired the wires may be provided with a screen or electromagnetic interference shield before the cable jacket is applied. Thus a cable may be formed in a continuous process by means well known in the art by braiding the wire bundle and extruding a cable jacket thereon. Any of the materials described above for the wire polymeric insulation may be used although halogen-free compositions e.g. compositions as described in the U.K. Patent Specifications Nos. 1,603,205 and 2,068,347A mentioned above are preferred. It is of course possible to employ additional means for providing integrity of the cable such as mica tape wraps, but these are not necessary nor are they desirable in view of the increased size and weight of the cable.

In certain circumstances it may be desirable to coat the oxide layer with a thin coating of a polymeric resin or lacquer in order to provide a barrier against water or electrolytes during service.

The present invention is especially suitable for forming flat cables which, as will be appreciated, are not susceptible to being wrapped with mica tape.

The present invention is especially suitable for forming flat cables which, as will be appreciated, are not susceptible to being wrapped with mica tape. Thus according to another aspect of the invention there is provided a flat cable which comprises a plurality of elongate metallic electrical conductors which have an adherent coating of an electrically insulating refractory oxide or nitride of a metal or semi-metal other than that from which the conductors are formed, the conductors being laid in side-by-side relationship and enclosed in a continuous polymeric cable insulating layer.

In many instances, the refractory coating described above will be the sole refractory present in the article. However, it is possible for the refractory described above to be used simply as a keying layer for the provision of a further refractory layer, and so, according to a yet further aspect the present invention provides an article of manufacture which has at least a part that is formed from a metal the article having, on a surface of that part, an adherent dense refractory keying layer and, on the keying layer, a further refractory layer that has been formed by a relatively fast deposition method.

By the phrase "relatively fast deposition method" is meant that the rate of deposition of the further refractory layer, measured for example in micrometers of thickness per unit time, is greater than the rate of deposition of the refractory keying layer. The properties of refractory coatings are known to depend significantly on the method by which they are formed or deposited onto a substrate, and in general, the techniques that exhibit the lowest deposition rates will form refractory layers having relatively high density, i.e. not being porous, and having higher adhesion to metallic substrates. Preferably the refractory keying layer has been formed by a vacuum deposition process, e.g. a sputtering, evaporation, ion plating, or chemical vapour deposition, for example any of those described above, and the further refractory layer preferably has been formed by a sol-gel deposition method, a plasma ashing method, a solution coating method or a plasma spraying method e.g. a flame spraying method, or may be formed by another, faster, vacuum deposition process.

According to the invention it is possible to form articles having a refractory coating which, although being relatively thick and so having good electrical insulation characteristics, also exhibits very good adhesion to the underlying metal even when subjected to mechanical or thermal stresses.

The further refractory layer preferably has a thickness of at least 0.5, more preferably at least 1 and especially at least 2 micrometers.

The refractory keying layer will usually be thinner than the further refractory layer, and preferably has a thickness of not more than 0.5 micrometers and most preferably not more than 0.3 micrometers, but usually at least 0.1 micrometers.

In order to optimise the adhesion between the refractory keying layer and the further refractory layer it is preferred for them both to have the same nominal chemical composition, that is to say, they both preferably have the same general chemical formula although, as explained below, the precise stoichiometry of one or both layers may differ from the stoichiometric formula.

After the keying layer has been formed, the further refractory insulating coating is applied. As stated above the further refractory insulating coating may be formed on the vacuum deposited refractory coating by any technique which is relatively fast, for example sol-gel, flame sprayed, or evaporated coatings.

The sol-gel process involves the hydrolysis and polycondensation of a metal alkoxide, for example, silicon tetraethoxide, titanium butoxide or aluminium butoxide to produce an inorganic oxide gel which is converted to an inorganic oxide glass by a low temperature heat treatment. The metal alkoxides can be used as precursors to inorganic glass preparation via the sol-gel route. The alumina gel can be prepared by adding an alkoxide of aluminium, such as aluminium secondary butoxide, to water which is heated to a temperature above 80° C. and stirred at high speed. Approximately two liters of water per mole of alkoxide are suitable quantities. The solution is maintained at 90° C. and approximately 0.5–1 hour after the addition of the alkoxide a quantity of acid, for example 0.07 moles of hydrochloric acid per mole of alkoxide, is added to peptise the sol particles. The sol is maintained at the boiling temperature to evaporate excess butanol and reflux conditions are established and maintained until peptisation is complete. The sols can be reduced in volume by removal of water until a viscosity suitable for wire coating is reached.

Wires are provided with the alumina gel for subsequent conversion to an inorganic insulation by a dip or extrusion process. In this process the wire is drawn through the gel prepared to a suitable viscosity, as described above, such that a controlled thickness of gel adheres to the wire. The thickness is best controlled by wiping excess gel from the wire using sizing dies. The gel coated wire then undergoes suitable drying and firing stages to convert the coating into an inorganic oxide glass. The precise conditions with respect to temperature and residence time in the various stages of conversion are dependent upon the gel composition prepared and its tolerance to relatively rapid changes in its environment. Porosity and integrity of the coating can be significantly affected by these stages. A suitable conversion process would include drawing the wire through drying ovens in which the temperature is controlled at approximately 80° C. and subsequently through progressive heat treatment stages which expose the wire for a few minutes to temperatures of 300° C. to 500° C. The required exposure times are dependent upon the initial thickness of the gel coating, but the general guidelines above are used with the recommendation that the drying process is carried out as slowly as practical. It may be desirable to build thickness in a multipass process in which several thin layers are deposited sequentially.

Flame (or plasma) spraying involves injecting a powder of the refractory compound into a high temperature, high velocity gas stream. This process occurs within a specially designed gun or torch, and the refractory compound is ejected as a molten or semi-molten spray. This spray condenses to form a dense refractory film when it strikes a substrate. The high temperature gas stream can be produced either by controlled burning of a combustible mixture of gases (e.g. acetylene and oxygen), or by striking a low voltage high current arc in an inert gas (e.g. argon) between metal electrodes.

Flame spraying torches are available commercially, and comprise a powder dispenser, gas flow controls, and a shaped nozzle. Several powder dispensing methods are used, including gravity and Archimedean screw. The gas temperature may reach several thousand °C. Plasma spraying is very similar to flame spraying, but the heat source is supplied by an electric arc. In addition to gas control, a special dc power supply is needed that can deliver up to 1000 A at 100 V. The cathode is often made of thoriated tungsten, and the anode is usually water-cooled copper. A plasma jet is blown out of the torch nozzle, and refractory powder is injected into this jet. The temperature of the plasma jet may be more than 10000° C., and the gas velocity is up to 1000 m/sec.

Several variations on the above methods exist including, for example, detonation gun coating and low pressure spraying. In a detonation gun, pulses of powder are melted and accelerated by the controlled explosion of acetylene-oxygen within a water-cooled cylindrical chamber. This hives high gas velocities (several thousand m/sec), leading to improved coating adhesion. Low pressure plasma spraying is similar to conventional plasma spraying, except the plasma jet (with molten powder) escapes into a rough vacuum, giving a denser, less contaminated coating.

After the keying layer and further refractory layer have been deposited on the wire conductor it may be desirable to coat the oxide layer with a thin coating of a polymeric resin or lacquer in order to provide mechanical protection and a barrier against water or electrolytes during service. Further polymeric insulation may then be extruded onto the coated conductor by methods well known in the art.

Where the sol-gel method is employed, it is possible in certain cases to dispense with the provision of a refractory keying layer, so that, according to a yet further aspect of the invention, ther is provided an electrical wire which comprises a copper conductor and an electrically insulating refractory coating at least part of which has been deposited on the conductor by a sol-gel method.

Although the invention has been described above with reference to the provision of insulating refractory materials, it is possible to use these techniques to provide the conductor with an electrically conductive inorganic compound, and accordingly the invention also provides an electrical component which comprises a metallic electrical conductor and a conductive layer formed from an electrically conductive inorganic metal compound, the conductive layer being bonded to the electrical conductor by an intermediate metallic or refractory layer.

The invention is applicable to many forms of electrical component in which an electrically conductive layer is provided in order to exhibit an electrical effect. The electrically conductive layer may be a semi-conductor, for example having an electrical resistivity from $10^3$ to $10^{10}$ ohm cm, or it may have a higher electrical conductivity, and may be either linear or non-linear in its electrical characteristics. For example in one form of device, the conductive layer may be formed from a material for example a doped ceramic such as an alkaline earth metal titanate, that exhibits a positive temperature coefficient of resistance (referred to hereinafter as a P.T.C. material) or it may exhibit a negative temperature coefficient of resistance (referred to hereinafter as an N.T.C. material). Such materials may have resistivities that vary through several orders of magnitude as the temperature of the material is raised through an interval of 10° to 50° C. Devices that utilise such P.T.C. materials may be used for instance as self limiting resistance heaters, circuit protection devices and the like. In some applications the conductive layer may be formed from a ferroelectric material or from a ferromagnetic material or from other curie point materials. Electrical conductors that are coated with ferromagnetic materials may be used as high frequency attenuation lines in which unwanted high frequencies are attenuated, while components having ferroelectric coatings may be used for example as skin effect heaters. Examples of ferroelectric materials include those ceramics of the general formula $AMO_3$ wherein A represents an alkaline earth metal, preferably barium, and M represents titanium, zirconium or hafnium; lithium niobate, lithium tantalate, lead titanate zirconate or lead metaniobate; and examples of ferromagnetic materials include ferrites, e.g. compounds of the general formula $MFe_2O_4$ wherein M represents for example iron ($Fe_3O_4$), nickel, cobalt or zinc; magnesium manganese ferrites and ferrochromates; magnetic iron oxides such as gamma $Fe_2O_3$ or certain oxides of chromium or nickel. In yet other applications, the conductive layer may have a voltage dependent resistivity, for example in the case of zinc oxide varistors and vanadium oxide devices. Other forms of voltage dependent device that may be made according to this invention include threshold and memory switching devices that use chalcogenide glass layers e.g. germanium-arsenic-tellurium-silicon glasses as described for example in U.S. Pat. No. 3,271,591, the disclosure of which is incorporated herein by reference.

As will be appreciated the above examples represent only a sample of the range of conductive layers that may be used for one reason or another in an electrical component.

Although such components are very useful in many circumstances, they often suffer from the disadvantage that it is difficult for the conductive coating to adhere well to the underlying metallic conductor with the result that the component is unable to withstand severe mechanical abuse. In other cases, even if the conductive coating does adhere satisfactorily to the metallic conductor, the ability of the component to withstand high temperatures e.g. above 200° C. or temperature cycling is severely limited. According to the present invention, however, the ability of the component to withstand mechanical abuse and/or temperature excursions may be significantly improved by the provision of an intermediate metallic or refractory layer.

BRIEF DESCRIPTION OF THE DRAWINGS

Several embodiments of the invention and a method of production thereof will now be described by way of example with reference to the accompanying drawings in which:

Referring to FIG. 1 of the drawings a 26 AWG stranded copper conductor formed from 19 copper strands 1 is coated with a 5 micrometer thick layer 2 of aluminium oxide by the reactive sputter ion plating method described above. A coating 3 based on a polyetherimide sold under the trade name "ULTEM" is then extruded on the oxide coated conductor to form a polymeric "insulating" layer of mean wall thickness 0.2 mm.

FIG. 2 shows a signal integrity cable formed by laying together seven wires shown in FIG. 1, forming an electromagnetic interference screen 4 about the bundle by braiding and then extruding thereon a jacket 5 based on a halogen-free composition as described in British Patent Specification No. 2,068,347 Example 1A.

The cable so formed is particularly lightweight and has a relatively small overall diameter in relation to the volume of the copper conductor.

Figure 3:
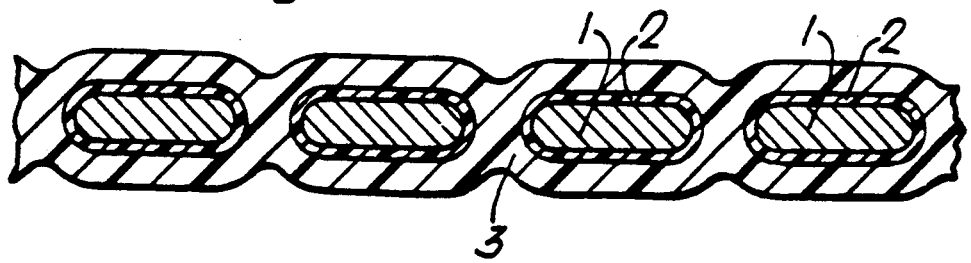
FIG. 3 is a cross-section through part of a flat conductor flat cable.

FIG. 3 shows a flat conductor flat cable comprising an array of flat copper conductors 1 with a 100 mil (2.54 mm) spacing. Each copper conductor 1 is provided with a 5 micrometer alumina coating as described above and the coated conductors are embedded in a single polymeric insulating layer formed from the polyether imide sold under the trade name "ULTEM"

Figure 4:
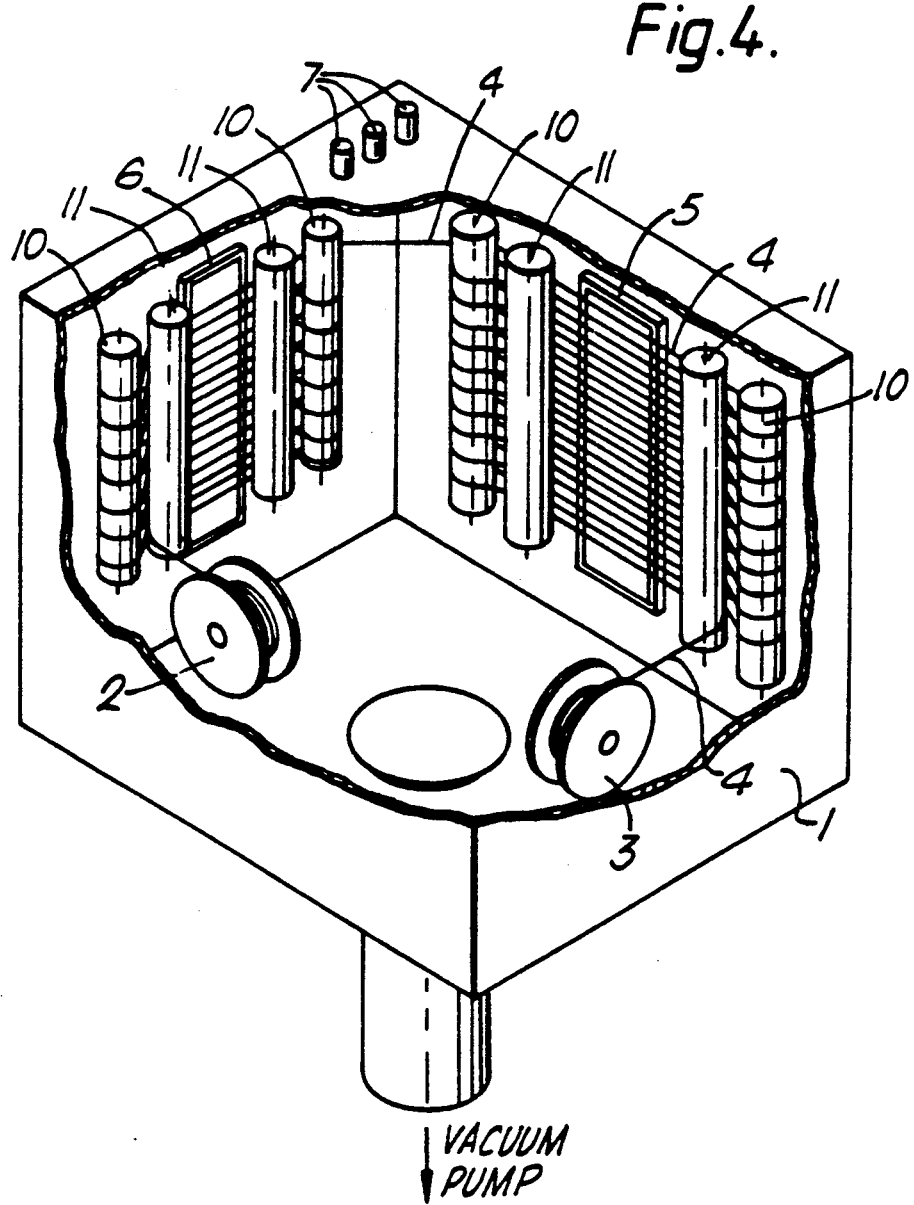
FIG. 4 is a schematic view of part of the sputtering apparatus showing its wire handling mechanism.

Apparatus for use in a batch process for coating wire conductor substrate is illustrated in FIG. 4. The apparatus comprises a vacuum chamber into which a complete wire transport mechanism which includes wire pay-off reel 2 and take-up reel 3, wire support rolls 10 and tensioning rolls 11 is loaded. The mechanism engages motor drives which control the passage of wire 4 so that the wire traverses a vertically mounted target 5 a number of times. Deposition occurs by the processes previously described. As before, variations in set-up are possible. An additional target (not shown) may be employed on the other side of the wire to increase coating rates and additional targets, e.g. target 6 can be employed to deposit intermediate layers before and/or after deposition of the primary oxide/nitride coating. Suitable design of the gas inlet system to suit the specific geometries employed can facilitate deposition of layers which have no defined boundaries as described previously. Batch length will depend on chamber dimensions and transport system design.

In the operation of such a batch process wire 4 is transferred from one reel 2 to the other 3 within the chamber. The route taken by the wire may cause it to pass before the smaller ancillary target 6 to deposit an intermediate layer of any desired material. Power to this target, combined with wire speed and the number of passes in front of the target will control the thickness of the intermediate layer deposit. The wire 4 may then pass in front of the larger primary target 5 to deposit the main coating. Again thickness will be dictated by a combination of power, wire speed and a number of passes. The ratio of thicknesses between the intermediate and the primary coating is controlled in the same way. Multi-layers can be built up by reversing the mechanism as desired such that the wire 4 passes back past the targets 5,6 in reverse order. Thickness and composition may be altered in the reverse pass as required, e.g the process employed at the smaller magnetron may be reactive on the reverse pass to deposit a compound of the metal on the intermediate layer, e.g. Ti and TiNx. Deposition of layers with no defined boundary between the metal intermediate layers (or substrates) and the oxide/nitride coatings may be achieved by setting up gradients of reactive gas in front of the primary target, such that wire at the top edge of the target 5 is subjected to deposition in an Argon rich atmosphere which gradually increases in reactive gas content as the wire progresses down the face of the target. A gradient can be achieved by a baffle system (not shown) which progressively leaks oxygen introduced at the bottom end of the target towards the upper end.

A simpler technique for producing the layer with no defined boundary involves use of a multipass process in which wire 4 is passed back and forth through the system, and with each pass the level of reactive gas is increased to a final level required to obtain the correct stoichiometry. Thus the stoichiometry of the intermediate layer increases in a series of small incremental steps from metal to required stoichiometry. Composite targets may also be used to produce intermediate layers with stoichiometry gradients. In the case of discrete articles, the articles may instead be held in front of the target by means of a rotating sample holder.

Figure 5:
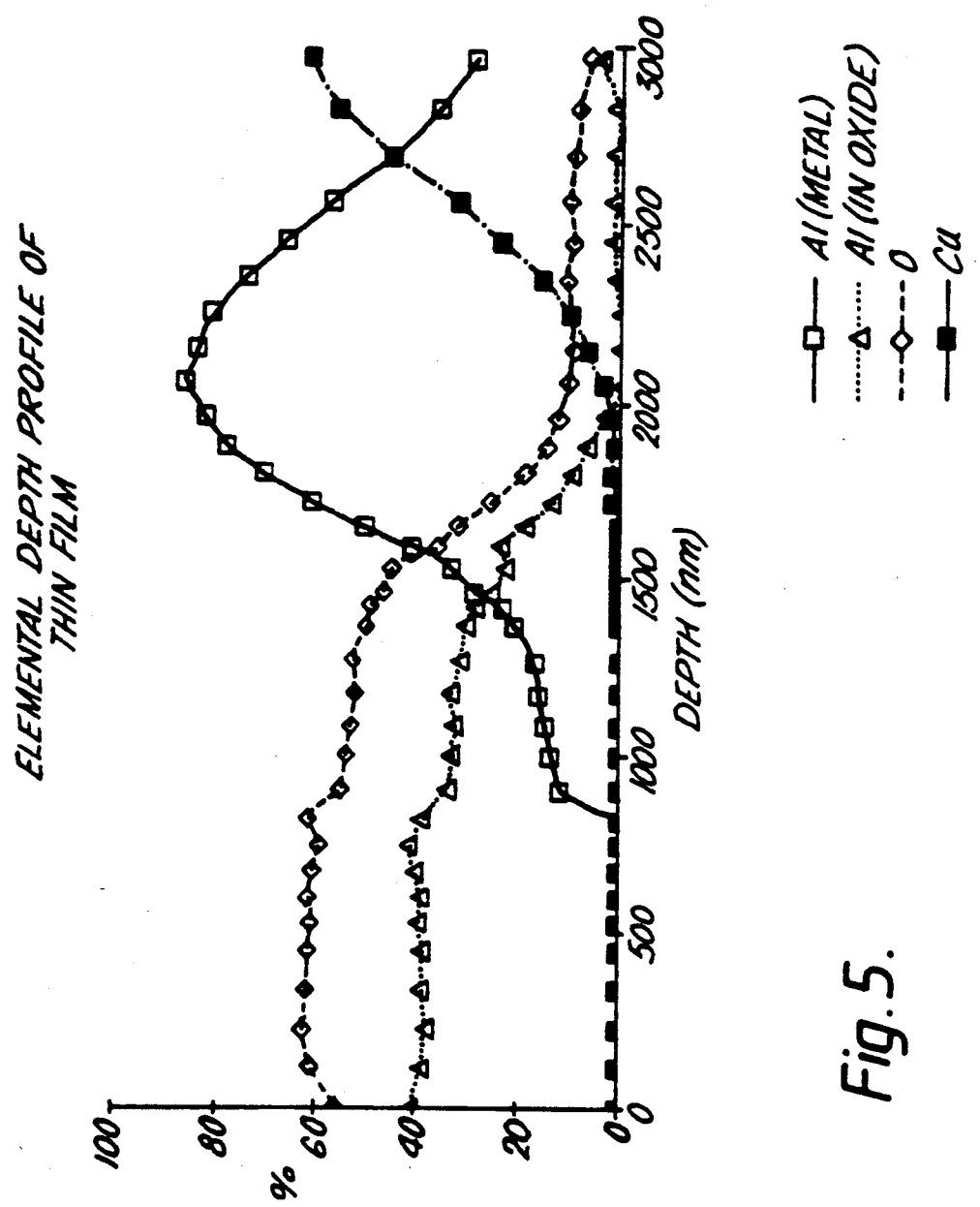
FIG. 5 is a graphical representation showing the variation in composition of the coating against thickness.

FIG. 5 is an Auger electron spectrogram for a coating having a 1 micrometer top layer of alumina, an intermediate region that varies in stoichiometry for about 0.7 micrometers to a metal intermediate layer of aluminium also measuring 0.7 micrometers. The film is deposited on a copper conductor.

Figure 6:
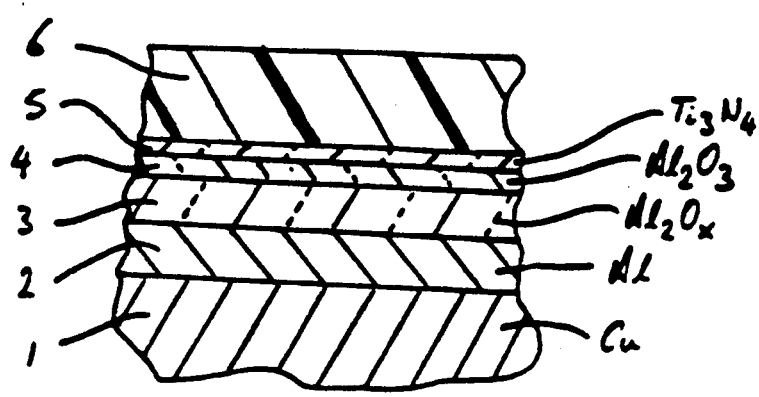
FIGS. 6 to 8 are schematic sections through parts of articles according to the invention.
Figure 7:
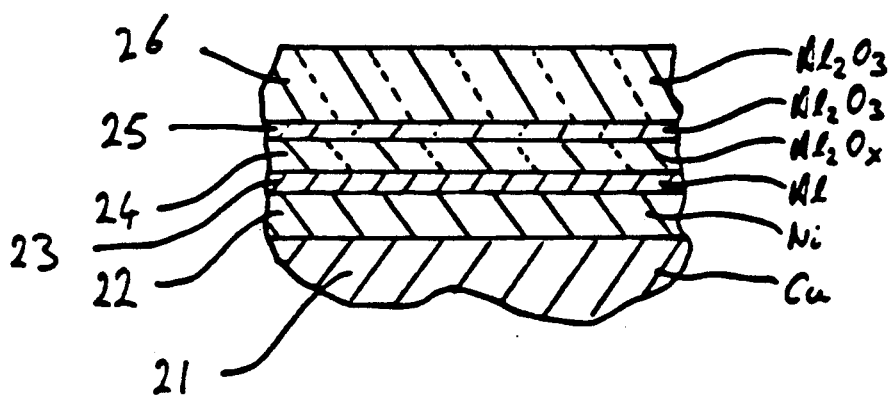
Figure 8:
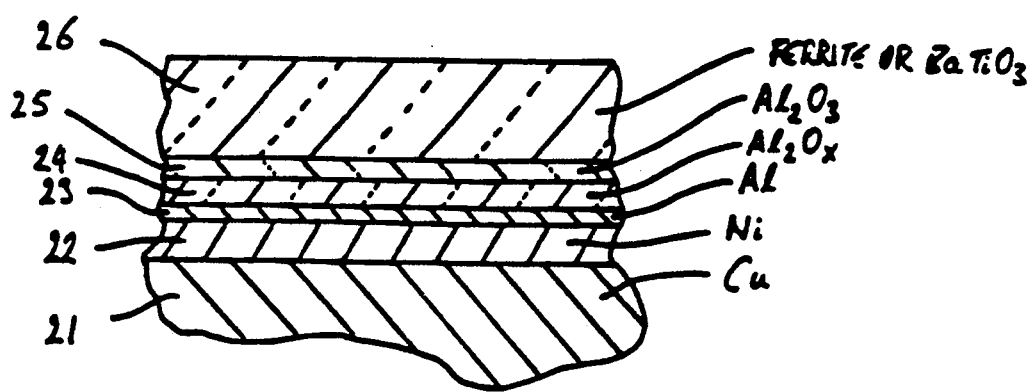

FIGS. 6 to 8 are schematic sections through parts of articles according to the invention showing typical arrangements of layers that may be formed on the copper substrate, the thickness of the layers being exaggerated for the sake of clarity.

As shown in FIG. 6 a copper substrate 1 is provided with a layer 2 of aluminium metal of a thickness of about 2 to 10 micrometers which may have been deposited for example by sputtering, electrodeposition or from the melt. A layer 3 of aluminium oxide $Al_2O_x$ is provided on the aluminium layer, the value of x varying from 0 in the region adjacent to the aluminium layer to 3 at the top surface, and a thin layer 4, e.g. about 3 micrometers in thickness, of stoichiometric aluminium oxide is deposited on the top surface of the aluminium layer. A further, thin, layer 5 of titanium nitride may be provided in order to increase the toughness of the article, followed by a relatively thick organic polymer layer 6.

Although the layers are clearly demarcated in the drawing by means of lines, it will be appreciated that such boundaries may, and preferably will, not be formed in practice, especially between the copper/aluminium, aluminium/$Al_2O_x$ and $Al_2O_x$/$Al_2O_3$ layers. Indeed, the aluminium, $Al_2O_x$ and stoichiometric alumina layers may all be formed in the same sputtering process in which case the stoichiometry of the layers will depend on the oxygen gradient used.

Another typical example is shown in FIG. 7 in which a copper substrate 21 is provided with a thick (e.g. 1 to 3 micrometers) layer 22 of nickel followed by a layer 23 of aluminium metal, a layer 24 of non-stoichiometric aluminium oxide $Al_2O_x$ and a layer 25 of stoichiometric aluminium oxide $Al_2O_3$, the layers 23, 24 and 25 having been formed e.g. by a sputtering method. An additional, relatively thick layer 26 of aluminium oxide (e.g. of about 5 to 15 micrometers thickness) may be deposited on the layer 25 by a non-vacuum deposition method for example by a sol-gel method.

FIG. 8 shows a modification of the article shown in FIG. 7 in which, instead of a thick top layer of alumina, a top layer 25 of ferrite or doped barium titanate (5 to 15 micrometers in thickness) has been deposited by an appropriate method.

Figure 1:
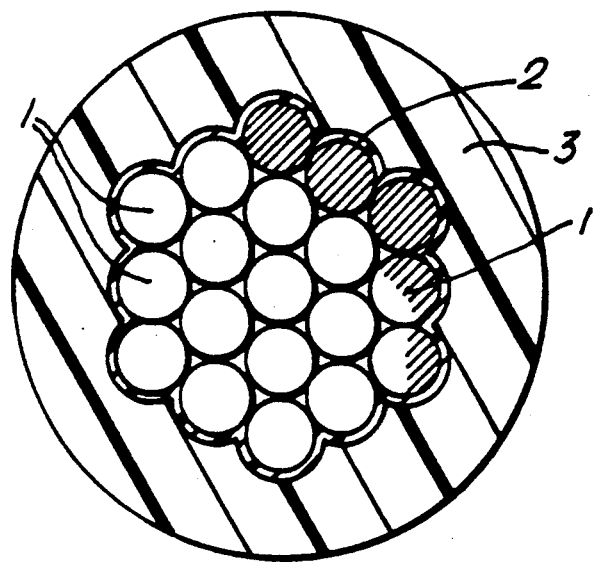
FIG. 1 is a cross-section through one form of wire according to the present invention.
Figure 9:
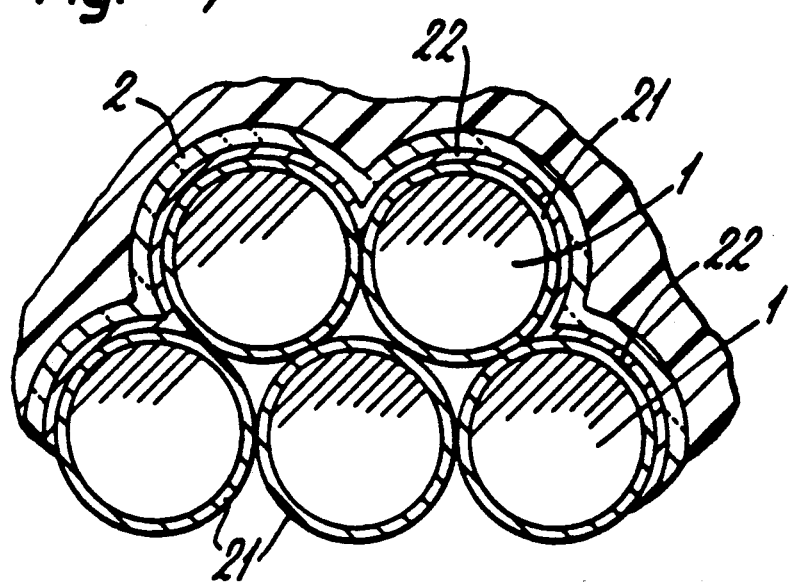
FIG. 9 shows part of a stranded conductor according to the invention.

FIG. 9 shows a preferred form of stranded conductor wire of the type shown in FIG. 1. Each of the copper strands is provided with a nickel coating 21 of approximately 1.5 micrometers thickness. Also, before the deposition of the alumina layer 2, the outer surface of the stranded conductor was provided with a 3 micrometer thick layer of aluminium 22.

The following Examples illustrate the invention:

EXAMPLES 1 and 2

Copper conductors were provided with an insulating aluminium oxide coating, approximately 2 micrometers thick, by use of the sputtering apparatus shown schematically in FIG. 4 of the drawings. The sputtering conditions were as follows: The wire 4 was precleaned by vapour degreasing in 1,1,1-trichloroethane prior to the deposition. The cleaning was achieved by passing wire continuously through the vapour in a vapour degreasing bath such that a residence time of 3 minutes was achieved. The wire 4 was then loaded into the vacuum chamber as shown in FIG. 4. The chamber was evacuated to a pressure of $1 \times 10^{-6}$ mbar prior to starting the process. At this stage Argon was admitted to attain a pressure of $1 \times 10^{-2}$ mbar whereupon a high frequency (300 kHz) bias potential was applied to the wire handling system which was isolated from ground. A bias potential of $-200$ V is achieved prior to transferring the wire 4 from reel 3 to reel 2 such that a residence time of 10 minutes was achieved. On completion of the cleaning cycle the pressure is reduced to $7 \times 10^{-3}$ mbar and the deposition process started.

4 kW of DC power was supplied to the aluminium target 5 which stabilises to a voltage of $-480$ volts. This voltage varied with sample geometries, target material and gas composition, e.g. on introducing oxygen gas to the system the target voltage will drop (in systems where power is the controlled parameter) as the oxygen reacts with the target to "poison" the surface. By careful closed loop monitoring and control of the system e.g. by quadrupole mass spectrometer sensing, the oxygen introduction was held such that just sufficient oxygen was introduced to react with the sputtered aluminium to form Alumina without signif-icantly poisoning the target. The oxygen level was held in balance such that the alumina deposited is as cose to full stoichiometry as possible. The wire passes from reel 2 to reel 3 being reactively coated as it passed the target 5. Residence time in this region was controlled by wire speed and adjusted to give the required thickness. The roller mechanism alternated the wire face exposed to the target as it progresses down the target length. Target 6 was not employed.

The coated conductors were then provided with a 0.25 mm insulating layer of low density polyethylene which was crosslinked by irradiation with high energy electrons to a dose of 20 Mrads.

The electrical performance of the insulated wires so formed was tested by twisting a pair of identical wires (2 twists per 2.5 cms length) to form a twisted pair cable of 1.5 m in length, connecting one end of the wires to a 1 MHz, 30 V square wave source and observing the wave across a 200 ohm load at the other end of the wires by means of an oscilloscope. The central section of the wires (about 0.5 m in length) was placed in an electric tube furnace and heated at a rate of 20° C. per minute. The temperature of the wires when the insulation fails was recorded. The wires were then allowed to cool and the insulation of the wire retested. It was noted that the polymeric insulation layer auto ignites at approximately 430° C., leaving only the thin oxide layer as insulation, which continued to function perfectly until the failure temperature indicated.

By way of comparison, the procedure was repeated, using wires insulated only by the crossliked polyethylene.

The results are shown in Table I, from which it may be seen that wires prepared according to the invention are superior to polymeric insulation both in regard to the temperature at which insulation is lost and by virtue of the reversibility of the loss on subsequent cooling.

TABLE I

| | Temperature of total insulation failure | Performance after cooling |
|---|---|---|
| EXAMPLE 1 | 500° C. | insulating |
| EXAMPLE 2 (Comparison) | 430° C. | conducting |

EXAMPLES 3 and 4

Examples 1 and 2 were repeated, with the exception that the twisted pair cables were subjected to heating in a propane gas burner having a flat flame 8 cm wide. The temperature of the flame just below the twisted pairs was maintained at 620° C. and the time to failure recorded.

The results are given in Table II, from which it may be seen tht wires according to the invention exhibit greater times to failure. The polymeric insulation burns away in the propane flame quickly, leaving the oxide layer as sole insulation until ultimate failure.

TABLE II

| | Time to failure in 620° C. propane flame |
|---|---|
| EXAMPLE 5 | 2 minutes |
| EXAMPLE 4 (Comparison) | 20 seconds |

EXAMPLES 5 to 7

In Example 5, Example 1 was repeated except that target 6 (FIG. 4) was employed to deposit a layer of aluminium metal onto the copper prior to the deposition of the aluminium oxide layer. Oxygen was supplied locally (and monitored locally) to target 5 to prevent contamination of target 6 which was shielded within the chamber. In Example 6 and 7 Example 5 was repeated with the exception that an oxygen gradient was established on target 5 to form an oxide layer intermediate between the metal interlayer (from target 6) and the oxide layer from the bottom of target 5. Twisted pair cables were tested in the tube furnace and in the propane gas burner as described in Examples 1 to 4.

In all the examples the top layers of uniform stoichiometry aluminium oxide had a thickness of approximately 2 micrometers. The results are given in Table III from which it may be seen that the presence of one or more interlayers significantly increases the temperature or time to insulation failure. As noted from Example I, the polymeric portion of the insulation auto ignited in the tube furnace at approximately 450° C., leaving the thin composite oxide layers to function as sole insulation until the indicated temperature of failure. Similarly, the polymeric portion quickly burned away in the propane flame

TABLE III

| Example No. | Aluminium layer micrometers | Aluminiumoxide intermediate layer, micrometers | Temperature total insulation failure (furnace test) | Time to failure in 620° C. deg. flame |
|---|---|---|---|---|
| 1 | 0 | 0 | 500° C. | — |
| 3 | 0 | 0 | — | 2 minutes |
| 5 | 0.2 | 0 | 750° C. | not |

TABLE III-continued

| Example No. | Aluminium layer micrometers | Aluminiumoxide intermediate layer, micrometers | Temperature total insulation failure (furnace test) | Time to failure in 620° C. deg. flame |
|---|---|---|---|---|
| | | | | measured |
| 6 | 0.3 | 0.3 | 800° C. | >30 mins |
| 7 | 0.3 | 0.3 | >750° C. | >30 mins* |

*flame temperature was 650 C. for this experiment.
Note: In Table III the inequality sign > signifies that the test was terminated at the time indicated, no failure of the insulation being recorded.

Example 7 was the same as Example 6, except that 7 strand 20 AWG wire was used. This example shows clearly that excellent high temperature insulation may be obtained even when only a portion of each outer strand is covered with the thin composite layer.

EXAMPLES 8 to 14

Copper conductors were provided with insulating oxide layers under the following conditions Example 6 as Example 1. Examples 7 to 9 as Example 5. Examples 10 to 12 as Example 6. The necessary adjustments to wire speed/wraps and hence residence time was adjusted to achieve the correct thicknesses of the various layers.

The DC electrical resistivity of the oxide layers was measured before and after heating the coated conductor to 900° C. for 30 seconds using a bunsen burner in poace of the propane burner of Examples 3 and 4. The oxide film ws observed after the heat exposure for adherence, cracks etc. The results are given in Table IV, from which it may be seen that by the use of interlayers (i.e. aluminium and varying stoichiometers of aluminium oxide) adhesion can be improved to the point where no spalling occurs, even at 900° C. and also films which are highly resistive before and after exposure to this temperature can be obtained.

gets 5, 6 were replaced with Titanium metal targets. The necessary adjustments to residence times were made for thickness control. Twisted pairs of these coated conductors were heated to 900° C. for 10 seconds. It was observed that coating remained intact, with no spalling and no copper migration through the layer.

EXAMPLE 16

Figure 2:
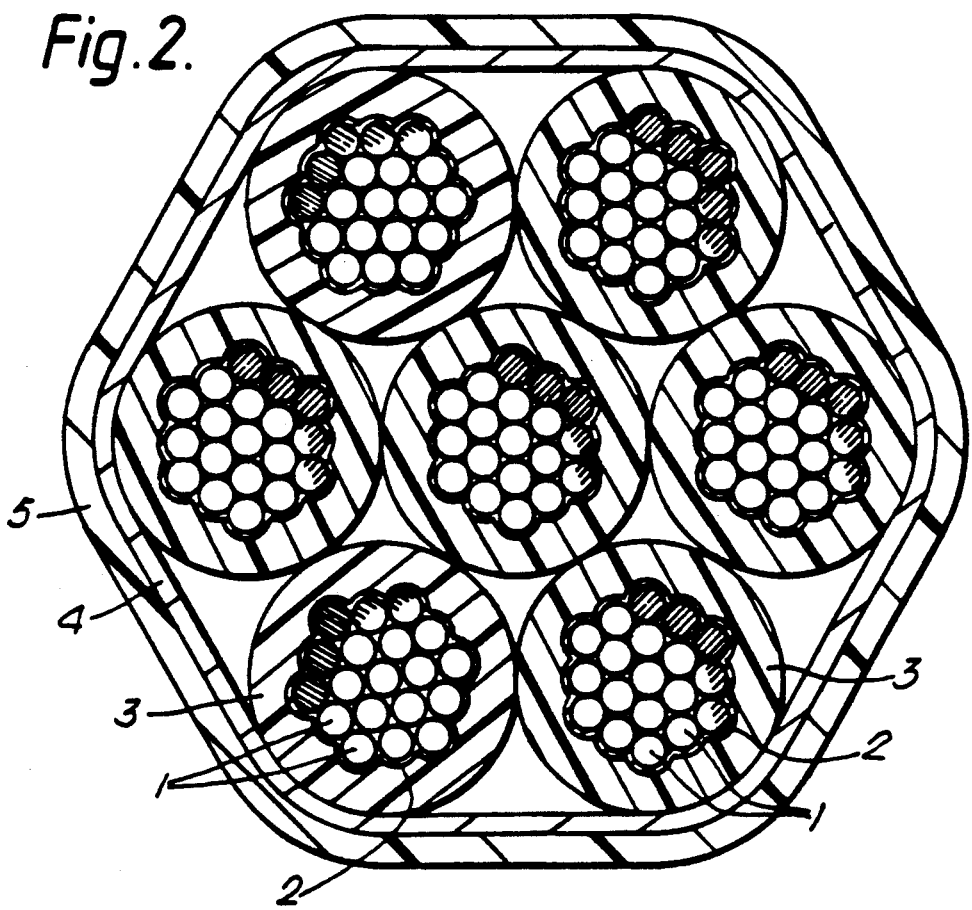
FIG. 2 is a cross-section through a signal integrity cable employing the wires of FIG. 1.

A cable formed as described above with reference to FIG. 2 was tested for its integrity by placing a length of it in a furnace at 800° C. and recording the length of time before a short circuit was formed between any two stranded conductors or between any stranded conductor and the shield 4 (IEE 331 test). No failure was recorded after 90 minutes.

EXAMPLE 17

Copper conductor were provided with a composite coating consisting of a first layer tantalum a top layer of tantalum oxide and an intermediate layer which varies in stoichiometry from metal to Ta2O5. Preparation is as Example 7. The metal interlayer measured 1.1 micrometers, combined intermediate and topcoats measured 2.3 micrometers.

D.C. electrical resistivity was measured as $2.5 \times 10^{13}$ ohm cm prior to exposing the sample to a bunsen flame of 900° C. for 30 seconds. D.C. resistivity upon cooling was measured as $1.3 \times 10^{12}$ ohm cm. The samples were also examined using a scanning electron microscope. No spalling or copper migration was noted.

The volume resistivity was also measured at elevated temperature in an apparatus which consists of a block of steel, heated by cartridge heaters, which formed one electrode of the measuring circuit, and a probe of known contact area which formed the other electrode. The components were housed in an earthed Faraday cage. The heating rate of the blockw as not uniform: it

TABLE IV

| EXAMPLE | ALUMINIUM LAYER, MICROMETERS | ALUMINIUM OXIDE INTERMEDIATE LAYER, MICROMETERS | ALUMINIUM OXIDE, TOP LAYER, MICROMETERS | RESISTIVITY BEFORE EXPOSURE OHM. CM. | RESISTIVITY AFTER EXPOSURE TO 900° C. 10 SECS. OHM. CM | OBSERVATIONS |
|---|---|---|---|---|---|---|
| 8 | 0 | 0 | 2.0 | $7 \times 10^{10}$ | fail[1] | Severe spalling, severe copper migration through layer. |
| 9 | 0.1 | 0 | 2.0 | $9 \times 10^{9}$ | fail[1] | slight spalling severe copper migration through layer |
| 10 | 0.6 | 0 | 1.9 | $2 \times 10^{11}$ | fail[1] | localised spalling |
| 11 | 1.0 | 0 | 2.0 | $3 \times 10^{10}$ | fail | localised spalling |
| 12 | 0.3 | 0.3 | 2.0 | $6 \times 10^{11}$ | $1 \times 10^{11}$ | some cracking but remains intact |
| 13 | 0.3 | 0.3 | 2.2 | $9 \times 10^{10}$ | $6 \times 10^{11}$ | some cracking but remains intact |
| 14 | 0.6 | 0.6 | 2.4 | $5 \times 10^{10}$ | $1 \times 10^{11}$ | some cracking but remains intact |

NOTE: [1]Fail = does not support 30 v

EXAMPLE 15

7 Strand 20 AWG copper conductors were provided with a composite coating consisting of a first layer of 2 micrometers of titanium, a second layer of 2 micrometers of graded stoichiometry TiOx in which x varied from 0 to 2, and a third layer of 2 micrometers of TiO2 prepared as Example 7 with the exception that the tarheated at approximataely 25° C./min up to about 400° C., decreasing steadily to about 10° C. thereafter. The limit of the apparatus was about 650° C. The volume resistivity was measured using a megohm meter made by Avo Ltd., of Dover, England, at a test voltage of 30 V D.C.

Using this apparatus, the volume resistivity was measured at frequent temperature intervals so that it was possible to measure the temperature at which the conductor insulation will no longer support 30 V, the curve being almost flat until this temperature. For the taltulum oxide coated conductors of Example 15, this fail temperature is 485° C.

EXAMPLE 18

Solid conductor was provided with a composite refractory coating as described in Example 6. An additional coating $TIN_x$ measuring 2 micrometers thick was subsequently sputtered onto the surface by the reactive process used in Example 6, with the exception that the aluminium target 5 is replaced with a titanium target 5. The reactive gas employed is nitrogen for this latter coat.

The scrape abrasion resistance of the coatings was compared with that of Example 6 using the following apparatus: a loaded blade was drawn repeatedly back and forth across the surface of the coated conductors at a frequency of 1 Hz, gradually wearing away the coatings as it did so. The blade was made of hardened steel, and had a radius of curvature of 0.225 mm; its stroke was 2.5 cm. The load used was 5N. Abraded samples were examined using an optical microscope, and failure was considered to have failed when the copper conductor became exposed. Example 6 failed after 23 blade cycles on average. Example 18 failed after 110 blade cycles on average. This improvement deminstrates that specific properties of coated conductors can be improved by the addition of extra protective layers.

EXAMPLE 19

Solid 20 AWG copper conductors were provided with a composite coating consisting of a first layer of 0.4 microns of titanium, a second layer of 0.4 micron graded stoichiometry $TiO_x$ and a third layer of 2 microns of $TiO_2$ prepared as in Example 15 with the necessary adjustments to residence time to control thickness. The conductors were heated in a bunsen flame to 900° C. for 30 seconds the film coating remained intact, with no spalling and no copper migration through the coating.

EXAMPLES 20 to 22

Copper conductors were provided with an insulating layer of aluminium oxide of varying thickness by RF sputtering from an alumina target using the following conditions. Preparation was followed as in Example 1. up to the start of the deposition process. At that stage Alumina was sputtered from an alumina target 5 onto the wire 4 as it passed from reel 2 to reel 3. Sputtering was achieved by raising the cathode assembly 5—Magnetron plus target—to a potential with respect to ground of −370 volts by application of 2.5 KW of power from a radio frequency generator. On striking a plasma the impedance was matched to reduce reflected power to less than 3%. Wire speed was adjusted to give the required thickness. Target 6 was not employed.

The temperature controlled volume resistivity rig described in Example 17 was used to determine the relationship between alumina thickness and fail temperature.

The results are given in Table V.

TABLE V

| EX- AMPLE | ALUMINA THICKNESS | FAILURE TEMPERATURE |
| --- | --- | --- |
| 20 | 0.7 microns | 375 C. |
| 21 | 1.3 microns | 410 C. |
| 22 | 15 microns | >650 C.* |

*Temperature limit of equipment.

These examples clearly demonstrate that the performance of the coated conductors can be altered at will by choice of the thickness of the insulation. It should be noted that the insulated conductors of Example 22 do not fail up to the limits of the test equipment and even at 650° C. the volume resistivity is $>10^8$ ohm cms.

EXAMPLE 23

Copper conductors were provided with an insulating layer of silica, of thickness 16 microns, by RF sputtering from a silica target using the same procedure as used for examples 20 to 22 with the exception that the alumina target 5 is replaced by a silica target 5.

The volume resisitivity fail temperature was measured as in Example 17 and is found to be greater than 650° C., the volume resisitivity at this temperature still being $10^8$ ohm cms.

EXAMPLES 24 to 27

7 strand 20 AWG copper conductors were provided with a composite coating consisting of a first layer of aluminium, a second layer of graded stoichiometry $Al_2O_x$ and a third layer of alumina prepared as in Example 7.

Twisted pairs of identical wires (2 twists per 2.5 cm length) were tested for signal integrity with a 1 MHZ 30 V square wave source, as described in Example 1, in a bunsen flame at 500° C. and at 700° C. The results are given in Table VI.

TABLE VI

| EXAMPLE | ALUMINIUM LAYER | ALUMINIUM OXIDE INTERMEDIATE | ALUMINIUM OXIDE TOP LAYER, MICRONS | TIME/TEMP TO FAILURE IN BUNSEN FLAME |
| --- | --- | --- | --- | --- |
| 24 | 0.4 | 0.4 | 0.65 | 23 mins/500° C. |
| 25 | 0.4 | 0.4 | 0.65 | 2 mins/700° C. |
| 26 | 0.4 | 0.4 | 1.9 | no failure after 30 mins/ 500° C. plus 30 mins/700° C. |
| 27 | 0.4 | 0.4 | 1.9 | 75 mins/700° C. |

By way of comparison, the procedure was repeated using wires insulated only by crosslinked polyethylene: a failure time of 20 seconds at 500° C. was measured.

These results clearly demonstrate that even very thin composite coatings made according to the invention survive for significant periods of time at 500° C. They also show that slightly thicker films (1.9 microns) can function for extended periods of time at significantly higher temperatures.

EXAMPLES 28 and 29

Copper conductors were provided with an insulating alumina layer by Rf sputtering from an alumina target using the conditions described in Examples 20 to 22.

They were then tested for signal integrity in a bunsen flame using the method described in Example 1, and the results are given in Table VII.

TABLE VII

| Example | Alumina thickness microns | Time/temp to failure in bunsen flame |
|---------|---------------------------|--------------------------------------|
| 28 | 2.9 | 10 mins/700° C* |
| 29 | 15 | 115 mins/850° C* |
| 30 | 15 | 150 mins/700° C** |

*failed due to copper migration
**test terminated without sample failure

These results clearly show the insulating qualities obtainable by coating conductors according to invention. They also show the very significant increase in lifetime at the elevated temperatures which may be obtained by use of a thicker film. Thus one is able to make a simple choice of insulation thickness for different operating environments.

By comparing Examples 27 and 28, it is possible to see the effect of the intermediate layer on insulation performance: from Example 28, one would expect that a short failure time (i.e. less than 10 mins at 700° C.) would be obtained using an alumina thickness of 1.9 microns. However, as already seen in Example 27, the composite coating which is thinner in total thickness as well as in the insulating portion, clearly and significantly out performs the coated conductor of Example 28. From examination of the failure specimens by scanning electron microscopy it is seen that both speciments of Example 28 and 29 by copper migration but that copper migration is severely hindered by presence of the interlayer, whereas in Example 27, no migration occurs.

Thus this comparison illustrates that the intermediate layers provide improved insulating performance under harsh thermal environment by significantly changing the failure mechanism.

EXAMPLE 31

Copper conductors were provided with an insulating silica layer of thickness 16 microns by RF sputtering from a silica target under the conditions described in Example 23.

They were then tested for signal integrity in a bunsen flame at 850° C.: failure was obtained only after exposure for 90 mins.

EXAMPLES 32-34

Copper conductors were provided with a 5 micrometer insulating alumina layer bound to the copper by an interlayer of pure metal 0.5 micrometers thick. The metal was either Aluminium in one case or titanium in another case. The aluminium interlayer case was demonstrated on both solid and stranded wire conductor. Deposition was as described in Example 5 with the exception that the insulating alumina layer is Rf sputtered as described in Example 16. Target 6 was replaced by titanium in the case of the titanium interlayer.

The wires were subjected to signal integrity testing as previously described at 700° C. The failure times are recorded in table VIII.

TABLE VIII

| EXAMPLE | WIRE TYPE | INTERLAYER | FAILURE TIME |
|---------|-----------|------------|--------------|
| 32 | 7 Strand 20 AWG | Aluminium | 61 minutes |
| 33 | Solid 20 AWG | Aluminium | 20 minutes |
| 34 | Solid 20 AWG | Titanium | 26 minutes |

The failure times when compared with Example 28 clearly illustrate the benefits of an interlayer for high temperature performance, even when an intermediate layer of varying stoichiometry as in Example 27 is absent. The data also demonstrates that the improvement is achieved even when using metal interlayers which differ from that of the metal oxide.

EXAMPLES 35-39

Examples 35 to 39 examine the onset temperature for the failure mechanism described as "copper migration". The examples use speciments described in earlier examples.
i.e.
Example 35 prepared as example 6
Example 36 prepared as example 14
Example 36 prepared as example 21
Example 38 prepared as example 28
Example 39 prepared as example 22

The test involved exposing specimens to high temperatures for short (1 minute) periods of time. A high temperature tube furnace was controlled to within a set temperature +1% with a sample pan situated in the centre of the oven. The pan was preheated to the set temperature prior to being pneumatically extracted for automatic sample loading and return to the oven. The sample pan temperature was accurately monitored and any temperature drop noted during loading was recovered within the 1 minute period. Loading time was 53 seconds.

Specimens of each example was exposed to a range of temperatures for the specified period and subsequently examined using a scanning electron microscope for the effect described as "conductor migration". The temperature at which the effect was first noted was recorded as the onset temperature.

| Example | Aluminium layer microns | Aluminium intermediate layer microns | Aluminium oxide top layer microns | Migration onset temperature |
|---------|-------------------------|--------------------------------------|-----------------------------------|------------------------------|
| 35 | 0.3 | 0.3 | 2 | 750° C. |
| 36 | 0.6 | 0.6 | 2.4 | 850° C. |
| 37 | 0 | 0 | 1.3 | <550° C. |
| 38 | 0 | 0 | 2.9 | 650° C. |
| 39 | 0 | 0 | 15 | >850° C. |

The Examples 35 to 39 illustrates 4 points. Firstly the surprisingly low temperature at which "conductor migration" occurs is demonstrated by Example 37 in which the effect is seen at a temperature approximately half that of the melting temperature of the conductor. Secondly, the benefit of incrased top coat thickness is demonstrated by Examples 37 to 39. Thirdly the benefits of an interlayer are seen by comparing Examples 35 and 36 with Example 38. By simply comparing topcoat thicknesses one would expect the Examples 35 and 36 to display onset temperatures lower than that for Example 38. In fact the opposite is shown thus demonstrating the effect of the interlayers. Fourthly, the benefits of increasing interlayer thickness are demonstrated by comparing Example 35 to Example 36.

EXAMPLE 40

19 strand 20 AWG copper wires were provided with an insulting alumina coating about 3 micrometers thick around their outer circumference by techniques described in Examples 20 to 22. On subjecting Example 40 to signal integrity testing as described in Example 3, except using a 700° C. flame, the time to circuit failure was recorded as 12 minutes. Wire insulated with only 0.2 mm of crosslinked polyethylene failed after 15 seconds under the same conditions. This example clearly shows that excellent high temperature insulation is obtained even when only a portion of each outer strand is covered with the thin refractory coating. Example 40 differs from previous multistrand wire examples in that the number of strands is increased to 19, thereby further reducing the portion of outer strand covered by the thin refractory coating.

EXAMPLE 41

7 strand 20 AWG copper wires were provided with a 1 micrometer coating of aluminium by sputtering as previously described for depositing the interlayer in Example 5. The wire was then subjected to a heat treatment by passing slowly through a tube furnace a 500° C. such that the residence time of 7 minutes is achieved. A highly adherent gold coloured copper/aluminium intermetallic layer is confirmed as having being formed by X-ray crystallography. The intermetallic covered wire is provided with a 5 micrometers thick coating of alumina by techniques described in Examples 20 to 22. Signal integrity testing as described in Example 40 results in signal failure after 46 minutes. This example clearly illustrates the benefits obtained by the presence of intermetallic layers intermediate to the conductor and insulation.

EXAMPLE 42

19 strand 20 AWG wires were provided with an insulting alumina coating 5 micrometers thick as described in Example 40. This Example differs from Example 40 by the presence of a conventionally applied tin coating as used frequently in the Wire and Cable Industry and the fact that the test temperature was 800° C. On subjecting the wires to signal integrity testing as described in Example 40 the following failure times were recorded.

Example 42: Tin Coated:166 minutes

It is believed that the exceptionally long survival time is due to the formtion of a tin/copper intermetallic layer.

EXAMPLES 43 To 49

Copper conductors were provided with aluminium intermediate layers of various thicknesses by use of the sputtering apparatus shown schematically in FIG. 4 of the drawings. The sputtering conditions were as follows: the wire 4 was precleaned by vapour degreasing in 1,1,1-trichloroethane prior to deposition. The cleaning was achieved by passing the wire through a vapour degreasing bath such that a residence time of 3 minutes was achieved. The wire 4 was then loaded into the vacuum chamber. The chamber was then evacuated to a pressure of $1 \times 10^{-6}$ mbar prior to starting the process.

At this stage argon was admitted to attain a pressure of $1.5 \times 10^{-2}$ mbar whereupon a high frequency (80 kHz) bias potential was applied to the wire handling system which was isolated from ground. A bias potential of $-850$ V was achieved, and the wire was transferred from reel 3 to reel 4 such that a residence time of 10 minutes was achieved. On completion of the cleaning cycle the pressure was reduced to $8 \times 10^{-3}$ mbar and the deposition process started.

3 kW of DC power was applied to the aluminium target 5. The wire passed from reel 2 to reel 3 being coated as it passed the target 5. Residence time in this region was controlled by wire speed and adjusted to give the required thicknesses. The roller mechanism alternated the wire face exposed to the target as it progressed down the target length.

Samples of copper conductor coated with aluminium as described above were subsequently coated with aluminium oxide in a similar process. For this second coating, an aluminium oxide target powered with an RF power supply was used. The wire residence time and target power were adjusted to give a constant thickness of aluminium oxide, being about 4 micrometers. During deposition of both aluminium and aluminium oxide the copper conductors were held at a negative bias potential relative to the chamber to promote adhesion. The D.C. dielectric strength of the refractory aluminium oxide layer was measured to be 57 volts/micrometer.

The electrical performance of the insulated wires so formed was tested by twisting a pair of identical wires (2 twists per 2.5 cms length) to form a twisted pair cable, connecting one end of the wires to a 1 MHz, 30 V square wave source and observing the wave across a 200 ohm load at the other end of the wires by means of an oscilloscope. The twisted pair cables were subjected to heating in a propane gas burner having a flat flame 8 cm wide. The temperature of the flame just below the twisted pairs was maintained at 900° C. and the time to failure recorded.

The results are given in Table IX, from which it may be seen that wires provided with intermediate layers beneath the refractory coating according to the invention exhibit significantly greater times to failure:

TABLE IX

| Example Number | Aluminium intermediate layer thickness (micrometers) | Time to failure in an 900° C. propane flame (minutes) |
| --- | --- | --- |
| 43 | 0 | 0.2 |
| 44 | 1 | 2.5 |
| 45 | 2 | 3.5 |
| 46 | 2.5 | 9.0 |
| 47 | 3.3 | 32 |
| 48 | 6.2 | 94 |
| 49 | 11 | 360* |

*Test terminated after 360 minutes with no failure observed.

The twisted pair samples were examined using optical and scanning electron microscopes after completion of the propane flame test. In the case of thicker intermediate layers, failure seemed to have occurred by migration of copper to form copper oxide, as described in the text. However, it was apparent that as the intermediate layer thickness increased, the circumferential cracking of the aluminium oxide decreased to the point where it was not detectable under 200× magnification. This reduction in crack formation is surprising in view of the fact that the aluminium intermediate layer has a higher thermal expansion mismatch with the aluminium oxide than does copper. In these cases migration proceeded either by slow diffusion through the refractory layer or by diffusion between wire strands. This progressive change in failure mode is reflected in the survival times observed.

EXAMPLE 50

7 strand 20 AWG copper conductors were provided with a composite coating consisting of a first layer of 2 micrometers of tantalum, a second layer of graded stoichiometry and a third layer of 2 micrometers of $Ta_2O_5$. The thickness of the first layer was 1:1 micrometers and the combined intermediate and top layer thickness was 2.3 micrometers.

The composite coatings were deposited by the use of reactive sputtering techniques and apparatus as described above.

D.C. electrical resistivity was measured as $2.5 \times 10^{13}$ ohm cm prior to exposing the sample to a bunsen flame of 900° C. for 30 seconds. D.C. resistivity upon cooling was measured as $1.3 \times 10^{12}$ ohm cm. The samples were also examined using a scanning electron microscope. No spalling or copper migration was noted.

The volume resistivity was also measured at elevated temperature in an apparatus which consists of a block of steel, heated by cartridge heaters, which formed one electrode of the measuring circuit, and a probe of known contact area which formed the other electrode. The components were housed in an earthed Faraday cage. The heating rate of the block was not uniform: it heated at approximately 25° C./min up to about 400° C., decreasing steadily to about 10° C. thereafter. The limit of the apparatus was about 650° C. The volume resistivity was measured using a megohm meter made by Avo Ltd., of Dover, England, at a test voltage of 30 V D.C.

Using this apparatus, the volume resistivity was measured at frequent temperature intervals so that it was possible to measure the temperature at which the conductor insulation will no longer support 30 V, the curve being almost flat until this temperature. This temperature was 485° C.

EXAMPLES 51 TO 54

19 strand, 22 AWG copper wire samples were provided with aluminium intermediate layers of different thicknesses as described in examples 43 to 49, followed by an aluminium oxide layer 4 micrometers thick.

The samples were suspended in air under slight spring tension and were tested by repeatedly passing through them a square wave 36A current pulse of 60 seconds duration separated by intervals of 45 seconds. This caused the samples to be temperature cycled up to about 750° C. and back again. The samples were observed with an optical microscope during this cycling, and the formation of copper oxide was noted. Results are shown in table X.

TABLE X

| Example | Al intermediate layer thickness (micrometers) | Notes |
| --- | --- | --- |
| 51 (comparison) | 1 | slight oxide formation after 1 cycle moderate oxide formation after 2 cycles severe oxide formation after 3 cycles |
| 52 | 3 | slight oxide formation after 2 cycles moderate oxide formation after 4 cycles |
| 53 | 12 | slight oxide formation after 14 cycles |
| 54 | 3* | test terminated after 50 cycles; oxide formation still only slight slight oxide formation noted after 100 cycles |

*This sample included an additional 1 micrometer layer of nickel between the copper and the aluminium.

The results demonstrate the increase in resistance to substrate oxidation as the thickness of the intermediate layer increases, and the added improvement obtained by the provision of an additional nickel layer.

EXAMPLES 55 AND 56

Figure 10:
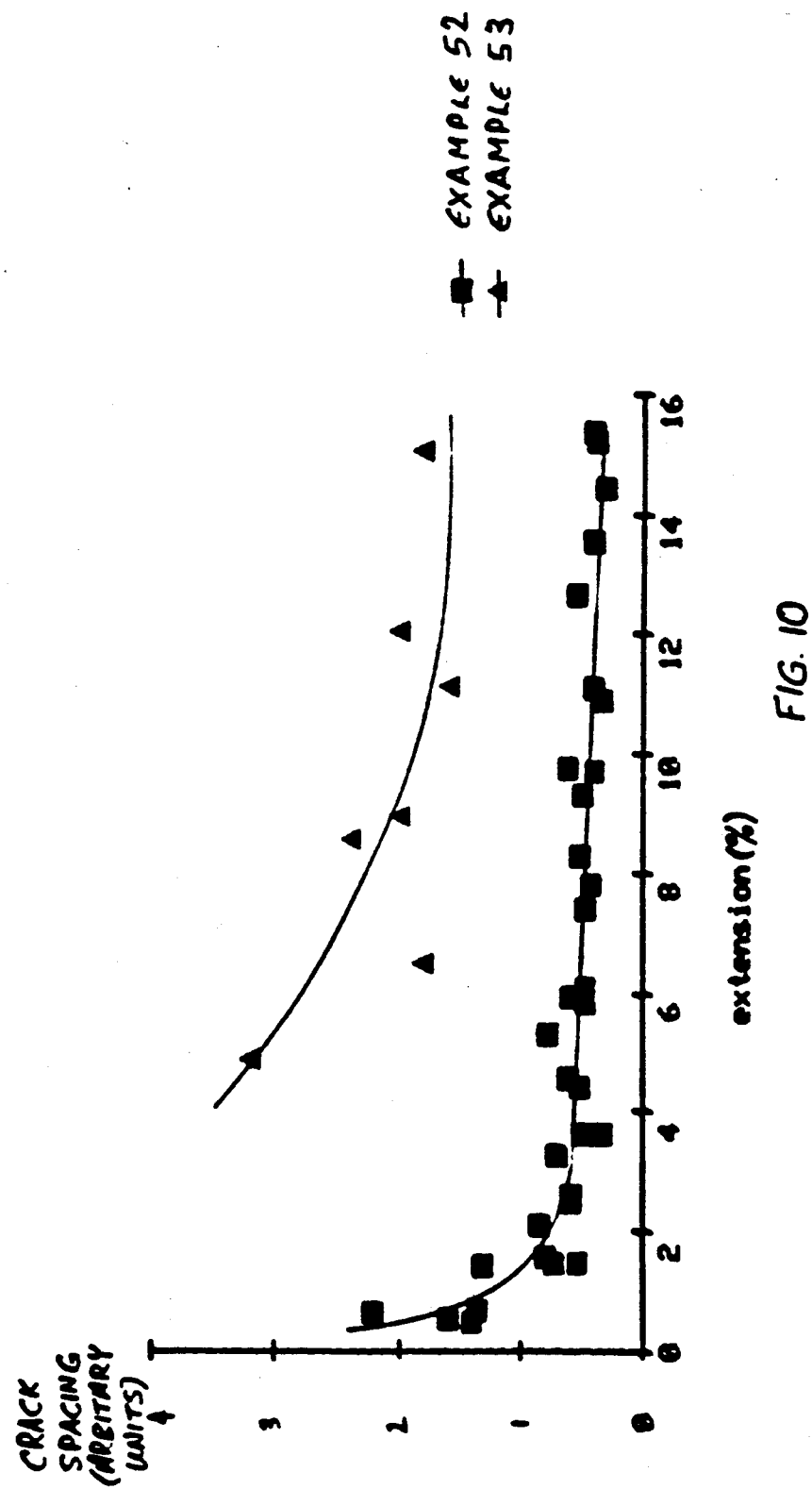
FIG. 10 shows graphically the amount of crack spacing versus extension in two wire samples of the present invention.

The wire samples prepared in examples 52 and 53 were subjected to a high tensile strain and the formation of cracks in the surface aluminium oxide layer was observed, and the results are shown graphically in FIG. 10. As the stain is increased the spacing between cracks, shown by the ordinate, decreases as the strain, shown by the abscissa, increases. It can be seen that, for any given strain, the number of cracks in the sample employing a 12 micrometer intermediate aluminium layer (example 53) was considerably smaller than the number of cracks in the sample employing a 3 micrometer intermediate aluminium layer (example 52). The reduction in crack density indicates a change in the detailed stress distribution in the refractory layer as the sample is stretched. This is thought to be an important feature in the reduction of spalling during mechanical abuse.

EXAMPLES 57 TO 59

Samples of 19 strand 22 AWG copper wire conductor were coated with aluminium intermediate layers as described in examples 43–49, and subsequently coated with refractory aluminium nitride. The nitride refractory layers were deposited by reactive sputtering from an aluminium target in an argon/nitrogen atmosphere at a total pressure of $8.10^{-3}$ mbar. The flow of nitrogen to the chamber was maintained so that stoichiometric aluminium nitride was deposited onto the conductor. The wire residence time and target power were adjusted so that the nitride refractory coating thickness was about 2 micrometers. The aluminium intermediate layers were of different thickness, as shown in table XI.

The dielectric strength of the refractory aluminium nitride layer was measured to be 108 V/$\mu$m.

The high temperature electrical performance of the insulated wires was tested as described in examples 43 to 49. The results are shown in table 3. It can be seen that wires provided with metallic intermediate layers beneath the nitride refractory coating perform significantly better at high temperatures.

The tested samples were examined with an optical microscope. Those with a thick aluminium intermediate layer (example 58) were seen to be in good condition, with no circumferential cracking of the nitride layer. Those with no intermediate layer (example 57) were badly cracked, and spalled away from the copper conductor.

TABLE XI

| Example | Aluminium intermediate layer thickness (micrometers) | Time to failure 900° C. propane flame (min) |
|---|---|---|
| 57 | 0 | 0.2 |
| 58 | 10 | 90 |
| 59 | 3* | 39 |

*This sample was provided with a layer of graded stoichiometry between the aluminium intermediate layer and the nitride refractory coating. The stoichiometry varied smoothly from aluminium metal to aluminium nitride, and the total thickness of the graded layer plus the stoichiometric nitride layer was about 2 micrometers.

EXAMPLES 60 AND 61

Refractory aluminium oxide coatings 3.5 micrometers thick were sputtered onto 19 strand 22 AWG copper wire conductors, some of which had been provided with an aluminium intermediate layer 3 micrometers thick according to the invention. The adhesion of the refractory layer to the underlying metal was assessed by observing the samples with an optical microscope whilst stretching them. At a particular strain, the adhesion of the refractory layer is overcome, and it spalls away from the underlying metal. The strain at which this occurred was noted; the results are given in table XII. It can be seen that it is possible to choose intermediate layers that significantly enhance the adhesion of the refractory layer to the underlying metal. It was observed that the refractory layer of Example 60 would spall away with gentle handling whereas the layer of Example 61 could withstand severe mechanical abuse without spalling.

TABLE XII

| Example | Aluminium intermediate layer thickness (micrometers) | Strain at spalling (%) |
|---|---|---|
| 60 (Comparison) | 0 | 1.6 |
| 61 | 3 | 6.7 |

EXAMPLES 62 AND 63

Samples of 19 strand 22 AWG copper wire conductors were sputter coated to a thickness of 5 micrometers with a refractory layer of silicon dioxide by RF sputtering from a silicon dioxide target. In some cases this refractory layer was applied directly to the copper conductor, in others the wires were provided with an aluminium intermediate layer 10 micrometers thick, manufactured as described in Examples 1 to 7. The high temperature electrical performance of twisted pairs of these wires was tested as described above. The results are shown in Table XIII, from which it can be seen that wires provided with a metallic intermediate layer perform significantly better than those without the intermediate layer. After testing, the wires were again examined with a microscope. It was found that the refractory layer of Example 62 (no intermediate layer) was badly cracked and spalled; that of Example 63 (with aluminium intermediate layer) was neither cracked nor spalled. Failure seemed to have occurred by slow growth of copper oxide between the strands.

TABLE XIII

| Example | Aluminium intermediate layer thickness (μm) | Time to failure in a 900° C. propane flame (min) |
|---|---|---|
| 62 (Comparison) | 0 | 1 |
| 63 | 10 | 142 |

EXAMPLE 64

Example 49 was repeated with the exception that the aluminium intermediate layer had a thickness of 10 micrometers and that the wire was provided with a cross-linked polyethylene/ethylene vinyl acetate copolymer blend insulation of 0.25 mm thickness. The wire survived 113 minutes before failure in a propane flame at a nominal temperature of 900° C. The temperature is given as a nominal temperature only in view of the uncontrolled temperature rise experienced by the wire as the polymeric insulation ignited.

EXAMPLES 65 TO 70

19 strand, 22 AWG copper wire which had been conventionally coated 360° around each strand with approximately 1.5 micrometers of nickel, and uncoated copper conductors were provided with aluminium intermediate layers of various thicknesses as described in Examples 43 to 49.

The results are given in Table XIV, from which it may be seen that nickel coated wires, and especially those provided with additional layers beneath the refractory coating according to the invention exhibit significantly greater times to failure:

TABLE XIV

| Example | Nickel intermediate layer thickness (micrometers) | Aluminium additional layer thickness (μm) | Time to failure in a 900° C. propane flame (mins) |
|---|---|---|---|
| 65 | 0 | 0 | 0.2 |
| 66 | 1.5 | 0 | 19 |
| 67 | 0 | 1 | 2.5 |
| 68 | 1.5 | 1 | 100 |
| 69 | 0 | 3.3 | 32 |
| 70 | 1.5 | 3 | 132* |

Note *Test terminated with no failure noted after 132 minutes

The results of all Examples 65 to 70 clearly illustrate the benefits to performance derived from increasing the thickness of the metallic intermediate layer beneath the refractory insulating layer. A progressive reduction in spalling and cracking of the refractory layer is also noticeable as the thickness of the metal interlayer increases. The additional benefits of coating the individual strands around their entire circumference is clear by comparison of Examples 65, 67 and 69 with Examples 66, 68 and 70 respectively. In Example 68 the total thickness of the metal intermediate layers beneath the refractory layer is less than that used in Example 69 yet a 3 fold improvement in failure time is recorded.

EXAMPLES 71 AND 72

In Example 7 a 22 AWG stranded copper conductor wire sample was provided with a 3 micrometer thick aluminium layer extending around its circumference (but not around the individual strands) followed by a 4 micrometer thick aluminium oxide layer using the procedure described in Examples 65 to 70.

The sample was then tested by repeatedly passing 36A square wave current pulses of 60 seconds duration through it separated by intervals of 45 seconds. This caused temperature cycling of the samples to a temperature of 750° C. The samples were observed using an optical microscope during the temperature cycling and the formation of copper oxide scale was monitored.

In Example 72, Example 71 was repeated with the exception that the individual strands of the copper conductor had previously been provided with a 1.3 micrometer thick nickel layer. The results are shown in Table XV from which it can be seen that the provision of the nickel layer around the individual strands considerably improves the resistance of the conductor to oxidation under the temperature cycling.

TABLE XV

| Example | Nickel layer thickness | Al layer thickness | Comments |
|---|---|---|---|
| 71 | — | 3 μm | slight oxide formation after 2 cycles |
| 72 | 1.3 μm | 3 μm | slight oxide formation noted after 100 cycles |

EXAMPLES 73 TO 77

19 strand 22 AWG copper wires, provided with conventionally-applied 360° nickel intermediate layers around each strand and sputter-coated with additional aluminium layers around the bundle but not around the individual strands, were manufactured to the dimensions shown in table XVI. In each case, a sputtered refractory silicon dioxide layer of thickness 5 micrometers was added. Twisted pairs of these wires were tested for their high temperature performance as described above. The results are shown in table XVI. Again, the benefits of intermediate and additional layers can be clearly seen.

TABLE XVI

| Example | Nickel intermediate layer thickness (μm) | Aluminium additional layer thickness (μm) | Time to failure in a 900° C. propane flame (min) |
|---|---|---|---|
| 73 | 0 | 0 | 1 |
| 74 | 1.5 | 0 | 13 |
| 75 | 0 | 3 | 3 |
| 76 | 1.5 | 3 | 24 |
| 77 | 0 | 10 | 142 |

EXAMPLES 78 to 80

19 strand 22 AWG copper wires, conventionally coated with 360° tin intermediate layers around each strand, and sputter coated with additional aluminium layers around the bundle but not around the individual strands, were manufactured to the dimensions shown in table XVII. In each case, a sputtered refractory aluminium oxide layer of thickness 5 micrometers was added. Twisted pairs of these coated wires were tested for their high temperature performance as described in examples 65 to 70, except the temperature of the propane flame was adjusted to 750° C. The results are shown in table XVII, from which it can be seen that wires provided with intermediate and additional layers according to the invention perform significantly better at high temperatures than those without. The wires of Example 80 were examined with an optical microscope after flame testing. They were seen to be in good condition: there was little cracking of the refractory coating, and copper oxide growth between the strands was minimal.

TABLE XVII

| Example | Tin intermediate layer thickness (micrometers) | Aluminium additional layer (micrometers) | Time to failure in a 750° C. propane flame (min) |
|---|---|---|---|
| 78 | 0 | 0 | 1 |
| 79 | 1 | 1 | 43 |
| 80 | 1 | 10 | >360* |

*Testing stopped with no failure noted.

EXAMPLES 81 TO 83

In Example 81 a copper conductor was provided with a 12 micrometer thick alumina coating by the sol-gel process described above, the coating being deposited directly onto the copper surface.

In Example 82, a copper conductor was provided with a 3.3 micrometer thick aluminium keying layer as described in Example 47.

The aluminium coated conductor was then provided with an alumina coating as described with respect to Example 81.

In Example 83 a copper conductor was provided with a 3.3 micrometer aluminium keying layer as described with respect to Example 82 and was subsequently coated with aluminium oxide in a similar process. For this second coating, an aluminium oxide target powered with an RF power supply was used. The wire residence time and target power were adjusted to give a constant thickness of aluminium oxide, being about 0.2 micrometers. During deposition of both aluminium and aluminium oxide the copper conductors were held at a bias potential relative to the chamber to promote adhesion.

The aluminium and alumina coated conductor was then provided with a sol-gel deposited alumina coating as in Example 81.

The samples were then tested to determine the adhesion of the top coat as follows. A fixed length of wire was subjected to a tensile strength whilst the strain was continuously recorded. During testing the wire sample was viewed through an optical microscope. When the coating was seen to significantly spall the strain was recorded. The strain value recorded at this point gave a measure of the adhesion of the coating. The composition of the samples and the results obtained are shown in Table No. XVIII.

TABLE XVIII

| Example | 81 | 82 | 83 |
|---|---|---|---|
| Sutstrate | 22 awg Stranded Copper | 22 awg Stranded Cu | 22 awg Stranded Cu |
| Metallic Aluminium layer (micrometers) | 0 | 3.3 | 3.3 |
| Vacuum deposited Aluminium Oxide Layer (micrometers) | 0 | 0 | 0.2 |
| Sol gel deposited Aluminium Oxide layer (micrometers) | 12 | 12 | 1 |
| Adhesion (arbitary units) | 0* | 415 | 600 |

*The adhesion of the coating to bare copper was very poor, rendering the samples unable to be tested due to immediate spalling.

The results show a clear improvement in adhesion of the gel derived alumina coating with the aluminium layer and a further improvement in adhesion with the vacuum deposited aluminium oxide layer.

EXAMPLES 84 TO 85

The electrical performance of wires prepared as those in Example 83, were tested by twisting pairs of identical wires (2 twists per 2.5 cms length) to form a twisted pair cable, connecting one end of the wires to a 1 MHz, 30 V square wave source and observing the wave across a 200 ohm load connected between the wires by means of an oscilloscope. The twisted pair cables were subjected to heating in a propane gas burner having a flat flame 8 cm wide. The temperature of the flame just below the twisted pairs was maintained at the required temperature and the time to failure recorded.

In Example 84 the sample was found to survive for 70 seconds in a flame at 900° C. In Example 85 the wires had still not failed after a flame exposure time of 72 minutes at 650° C. The substrate material onto which the sol-gel derived aluminium oxide was deposited for Examples 84 and 85 had a dense 0.2 micrometers coating of vacuum deposited aluminium oxide on its surface. Although this layer is insulating, it was incapable of supporting 30 V at room temperature.

EXAMPLES 86 TO 88

22 AWG 19 strand copper wire conductors were provided with sputtered aluminium and aluminium oxide layers using the method detailed in examples 81 and 82. The wires were then transferred to another vacuum chamber equipped with a 25 kW electron beam gun. This chamber was pumped down to a base pressure of $5.10^{-5}$ mbar, and a further refractory insulating layer of aluminium oxide deposited by electron beam evaporation. The electron beam power was about 6 kW (25 kV, 240 mA), and the refractory was evaporated directly from highly sintered alumina pieces, contained in a water-cooled copper crucible. The deposition rate of aluminium oxide by evaporation was about 3 $\mu$m/min, much faster than the refractory keying layer deposition rate, which was about 0.01 $\mu$m/min.

Samples manufactured as described above were adhesion tested using the tensile method described in examples 81 and 82. The results are given in Table XIX, from which it is clear that a thin refractory keying layer deposited by a relatively slow method improved the adhesion of a further refractory layer deposited by a faster method.

TABLE XIX

| Example | Al intermediate layer thickness ($\mu$m) | Al$_2$O$_3$ keying layer thickness ($\mu$m) | Al$_2$O$_3$ further layer thickness ($\mu$m) | Adhesion (arbitary units) |
|---|---|---|---|---|
| 86 | 0 | 0 | 7 | 500 |
| 87 | 0 | 0.5 | 7 | 1200 |
| 88 | 7 | 0.5 | 7 | 2150 |

The wire of Example 88 was tested for electrical performance as described in Example 84 (900° C.) and no failure was recorded after 4 hours, whereas the wire of Example 86 could not be tested due to immediate spalling.

EXAMPLES 89 AND 90

19 strand, 22 AWG copper wire conductors were provided with a 4 micrometers thick titanium intermediate layer by use of the sputtering apparatus shown schematically in FIG. 4 of the drawings. The sputtering conditions were as described in Examples 43 to 49 with the exception that a titanium target 5 was used to which 4 kW of D.C. power was applied.

The titanium-coated wire was then coated with a substoichiometric oxide of titanium, TiO$_x$, by reversing the wire handling apparatus, and reactively sputtering the titanium target in an argon/oxygen atmosphere. By way of comparison, bare copper wire (with no Ti intermediate layer) was also coated with TiO$_x$. Both Ti and TiO$_x$ layers surrounded the bundles of copper stands, but not each individual strand. The samples were assessed for the adhesion of the TiO$_x$ layer, and the results are given in Table XX.

TABLE XX

| Example | Ti layer thickness ($\mu$m) | TiO$_x$ layer thickness ($\mu$m) | Adhesion |
|---|---|---|---|
| 89 | 0 | 4 | Very poor coating spalled with minimal handling. |
| 90 | 4 | 4 | Excellent; survived severe mechanical abuse without detectably spalling (tight knotting of wire). |

The ability of examples 89 and 90 to withstand thermal cycling was also tested. Square wave current pulses (30A, 60 seconds on, 30 seconds off) were repeatedly passed down the wire samples, which heated them from 25° C. to 350° C. and back again. The TiO$_x$ coating of examples 89 was seen to spall away from the conductor after 1 cycle, whereas example 90 remained completely intact even after 10 cycles.

The results show that the Ti intermediate layer significantly improves the adhesion of the TiO$_x$ to the copper wire.

The electrical properties of the sputtered TiO$_x$ were investigated by coating a flat copper strip with 4 um Ti plus 4 um TiO$_x$. The current/voltage relationship of the TiO$_x$ was measured using a variable voltage DC power supply and an ammeter, making contact to the TiO$_x$ film via an electrode made of silver-loaded conductive paint. A non-linear relationship between current and voltage was found, and the TiO$_x$ had a negative temperature coefficient of resistance (i.e. the TiO$_x$ was an NTC material). The resistivity of the TiO$_x$ film was found to be $7.10^7$ cm with an applied potential of IV (lower with higher potential).

EXAMPLES 91 AND 92

19 strand, 22 AWG copper wire conductors were coated with layers of Ni and NiO as shown in Table XXI. The sputtering method described above was used to manufacture these samples. NiO is an antiferromagnetic material at room temperature.

The samples were then tested to determine the adhesion of the top coat as follows. A fixed length of wire was subjected to a tensile stress whilst the strain was continuously recorded. During testing the wire sample was viewed through an optical microscope. When the coating was seen to spall significantly the strain was recorded. The strain value recorded at this point gave a measure of the adhesion at the coating. The results of this adhesion testing are also given in Table XXI.

TABLE XXI

| Example | Ni layer thickness ($\mu$m) | NiO layer thickness ($\mu$m) | Adhesion (arbitary units) |
|---------|---|---|-----|
| 91 | 0 | 4 | 600 |
| 92 | 0.5 | 4 | * |

*no failure observed, even when the wires were stretched beyond their breaking strain.

Examples 91 and 92 were also subjected to the thermal cycling test described above. Again, Example 91 (no Ni intermediate layer) was seen to spall after 1 cycle, but Example 92 (0.5 $\mu$m Ni intermediate layer) was intact after 10 cycles.

EXAMPLES 93 AND 94

Flat copper conductors were sputter coated with a 4 um titanium intermediate layer, and subsequently coated with Si-doped barium titanate by thermal evaporation. The evaporation process used was as follows: pieces of Si-doped barium titanate were loaded into a molybdenum crucible, and the vacuum chamber pumped down to about $10^{-4}$ mbar The power supply to the crucible was then switched on, heating the evaporant. When the heating current reached about 280A, the charge started to evaporate. Heating was continued for about 12 minutes, during which time Si-doped BaTiO$_3$ was deposited onto the Ti-coated copper substrates (which were held about 20 cm above the crucible). Using this method, films about 0.3 um thick were deposited. To form a comparison, bare copper substrates (with no Ti intermediate layer) were also coated.

The adhesion of the Si-doped BaTiO$_3$ films was tested by heating the coated flat conductors to about 500° C. for 1 minute. On cooling, the titanate film had spalled away from the bare copper substrates, exposing copper that had oxidised in places. In contrast, those samples provided with the 4 um Ti intermediate layer remained undamaged.

Examples 89 to 94 clearly demonstrate that the adhesion of inorganic metal compounds to metallic substrates can be significantly improved by the use of intermediate layers.

We claim:

1. An electrical wire which comprises an elongate metallic electrical conductor having an adherent coating of a refractory compound of a metal or semi-metal that is bonded to the conductor by a metallic or refractory intermediate layer, the stoichiometry of the refractory coating varying throughout its thickness such that the proportion of metal or semi-metal in the coating decreases toward the outer surface of the coating, and, surrounding the coated conductor, a layer of polymeric insulation.

2. A wire as claimed in claim 1, wherein the intermediate layer comprises a metal.

3. A wire as claimed in claim 2, wherein the intermediate layer comprises that metal from which the refractory coating is formed.

4. A wire as claimed in claim 2, wherein the intermediate layer comprises nickel or silver.

5. A wire as claimed in claim 1, wherein the adherent coating comprises an oxide or nitride of a metal or semi-metal.

6. A wire as claimed in claim 5, wherein the adherent coating comprises an oxide of aluminium, silicon, titanium or tantalum.

7. A wire as claimed in claim 1, wherein the refractory coating contains the metal or semi-metal in a stoichiometric excess.

8. A wire as claimed in claim 1, wherein the coating has an outer region of substantially uniform stoichiometry.

9. A wire as claimed in claim 1, wherein the refractory coating has been formed by a vacuum deposition process.

10. A wire as claimed in claim 9, wherein the refractory coating has been formed by a reactive sputter ion plating method.

11. A wire as claimed in claim 1, wherein at least part of the refractory coating has been formed by a sol-gel method.

12. A wire as claimed in claim 1, which comprises a layer of aluminum nitride or titanium nitride which has been deposited on top of the refractory coating.

13. A wire as claimed in claim 1, wherein the refractory coating comprises an oxide, and has a refractory nitride layer thereon.

14. A wire as claimed in claim 1, wherein the metallic electrical conductor has a melting point of at least 800° C.

15. A wire as claimed in claim 14, wherein the metallic electrical conductor comprises copper.

16. A wire as claimed in claim 15, wherein the intermediate layer is formed from a metal that acts as a barrier to diffusion of oxygen or copper or both so that migration of copper through the refractory layer when the article is heated is suppressed.

17. A wire as claimed in claim 16, wherein the intermediate layer is formed from aluminium, silicon, titanium, tantalum, nickel, manganese, chromium or an alloy thereof.

18. A wire as claimed in claim 1, wherein the refractory coating has a thickness in the range of from 0.5 to 15 micrometers.

19. A wire as claimed in claim 1, wherein the conductor comprises a bundle of strands and the refractory coating extends around the circumference of the bundle but not around the individual strands.

20. A wire as claimed in claim 19, wherein the intermediate layer has a thickness of at least 1.1 micrometers.

21. A wire as claimed in claim 20, wherein the intermediate layer has a thickness of at least 2 micrometers.

22. A wire as claimed in claim 1, wherein the intermediate layer has a thickness of at least 1.1 micrometers.

23. A wire as claimed in claim 22, wherein the intermediate layer has a thickness of 2 micrometers.

24. A wire as claimed in claim 1 wherein the polymeric insulation has been crosslinked.

25. A wire as claimed in claim 1, wherein the polymeric insulation has been crosslinked by irradiation.

26. A wire as claimed in claim 1, wherein the polymeric insulation contains an inorganic filler.

27. An electrical wire which comprises an elongate metallic electrical conductor having an adherent coating of a refractory compound of a metal or semi-metal that is bonded to the conductor by a metallic or refractory intermediate layer, and, surrounding the coated conductor, a layer of substantially halogen-free polymeric insulation.

* * * * *